(12) United States Patent
Fencl et al.

(10) Patent No.: US 6,500,267 B1
(45) Date of Patent: Dec. 31, 2002

(54) REDUCTION OF ENERGY CONSUMPTION IN A COOLING OR HEATING SYSTEM THROUGH UVC IRRADIATION

(75) Inventors: Forrest B. Fencl, Huntington Beach; Robert Scheir, Sherman Oaks, both of CA (US)

(73) Assignee: Net Zero, Inc., Westlake Village, CA (US)

( * ) Notice: Subject to any disclaimer, the term of this patent is extended or adjusted under 35 U.S.C. 154(b) by 0 days.

(21) Appl. No.: 09/167,376

(22) Filed: Oct. 6, 1998

(51) Int. Cl.$^7$ ................................................ A61L 2/10
(52) U.S. Cl. ............................................. 134/1; 422/24
(58) Field of Search ........................... 134/1; 422/121, 422/29, 186.3; 55/279; 62/78

(56) References Cited

U.S. PATENT DOCUMENTS

| | | | |
|---|---|---|---|
| 3,744,216 A | 7/1973 | Halloran | 55/102 |
| 3,926,556 A | 12/1975 | Boucher | 21/54 |
| 4,786,812 A | 11/1988 | Humphreys | 250/455.1 |
| 4,867,796 A * | 9/1989 | Asmus et al. | 134/1 |
| 4,885,047 A * | 12/1989 | Ury et al. | 134/1 |
| 4,990,313 A | 2/1991 | Pacosz | 422/121 |
| 5,112,370 A | 5/1992 | Gazzano | 55/102 |
| 5,151,135 A * | 9/1992 | Magee et al. | 134/1 |
| 5,207,074 A | 5/1993 | Cox et al. | 62/285 |
| 5,215,592 A * | 6/1993 | Jackson | 134/1 |
| 5,225,000 A * | 7/1993 | Fujii et al. | 134/1 |
| 5,225,167 A | 7/1993 | Wetzel | 422/121 |
| 5,247,178 A | 9/1993 | Ury et al. | 250/483 |
| 5,322,569 A * | 6/1994 | Titus et al. | 134/1 |
| 5,330,722 A | 7/1994 | Pick et al. | 422/121 |
| 5,334,347 A | 8/1994 | Hollander | 422/24 |
| 5,453,049 A | 9/1995 | Tillman, Jr. et al. | 454/228 |
| 5,482,561 A * | 1/1996 | Yeung et al. | 134/1 |
| 5,492,557 A | 2/1996 | Vanella | 96/16 |
| 5,523,057 A | 6/1996 | Mazzilli | 422/121 |
| 5,558,158 A | 9/1996 | Elmore | 165/122 |
| 5,643,472 A * | 7/1997 | Engelsberg et al. | 216/65 |
| 6,245,293 B1 | 6/2001 | Fencl et al. | |
| 6,267,924 B1 | 7/2001 | Fencl et al. | |
| 6,280,686 B1 | 8/2001 | Scheir et al. | |
| 6,313,470 B1 | 11/2001 | Fencl et al. | |

FOREIGN PATENT DOCUMENTS

WO    WO9517634    6/1995

\* cited by examiner

*Primary Examiner*—Randy Gulakowski
*Assistant Examiner*—Saeed Chaudhry
(74) *Attorney, Agent, or Firm*—Steven C. Sereboff; So Cal IP Law Group

(57) ABSTRACT

There are described apparatus and methods wherein ultraviolet light kills and/or degrades and vaporizes microorganisms and organic material which naturally form over time on a heat exchanger. As this matter is eliminated, the pressure drop is decreased (i.e., airflow is increased) and the heat exchange efficiency (capacity) is increased. Less energy per Btu removed is used by the cooling system, and less energy is used by the HVAC system to move air.

25 Claims, 18 Drawing Sheets

US 6,500,267 B1

REDUCTION OF ENERGY CONSUMPTION IN A COOLING OR HEATING SYSTEM THROUGH UVC IRRADIATION

CROSS-REFERENCE TO RELATED APPLICATIONS

This application is a continuation in part of Application No. 08/803,350 filed Feb. 20, 1997 entitled "Method of UV Distribution in an Air Handling System," issued Oct. 6, 1998 as U.S. Pat. No. 5,817,276, which is incorporated herein by reference.

This application is related to application Ser. No. 08/773,643, filed Dec. 24, 1996 entitled "Single-Ended Germicidal Lamp for HVAC Systems" issued Feb. 2, 1999 as U.S. Pat. No. 5,866,076 which is incorporated herein by reference.

This application is related to Application No. 09/170,361 having the same inventors as this application and filed Oct. 13, 1998 entitled 'Returning A Heat Exchanger Efficiency To "As New"' issued Nov. 6, 2001 as U.S. Pat. No. 6,313,470. This application is related to the following applications having the same inventors as this application and filed Oct. 14, 1998: Application No. 09/173,081 entitled "Reduction of Pressure Drop of a Cooling or Heating System" issued Jul. 31, 2001 as U.S. Pat. No. 6,267,924; Application No. 09/172,638 entitled "Control of Health Hazards in an Air Handler" issued Aug. 28, 2001 as U.S. Pat. No. 6,280,686 and Application No. 09/172,637 entitled "Cleaning and Maintaining a Drain Pan in an Air Handling System" issued Jun. 12, 2001 as U.S. Pat. No. 6,245,293 which is a continuation-in-part of this application.

This application is related to several other applications having the same inventors as this application and filed either concurrently with this application or shortly after the filing of the application.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure, as it appears in the Patent and Trademark Office patent files or records, but otherwise reserves all copyright and trade dress rights whatsoever.

BACKGROUND OF THE INVENTION

1. Field of the Invention

The present invention relates generally to the reduction of energy usage in cooling and heating systems and more particularly to minimizing air horsepower and maximizing the operating performance of heat exchangers in cooling and heating systems.

2. Description of Related Art

One mature industry that is economically sensitive to costs is the heating, ventilation and air conditioning (HVAC) industry. Because of the competitive nature of both the construction and HVAC industries, HVAC systems must be inexpensive to install. Of a more global interest though, is the cost to operate and maintain HVAC systems. Often, a building owner will replace an aging HVAC system as the reduction in operating and maintenance costs can offset the retrofit cost, sometimes in a matter of months.

Broad social and energy policies also favor more efficient HVAC systems. In these days of electricity deregulation and conservation, it has become even more important to conserve energy consumption. Recently, entire electrical grids have shut down on very hot days in part because of the huge demand of HVAC systems running at extreme capacity. Furthermore, energy conservation translates directly into improved environmental conditions and decreased reliance upon foreign petroleum.

HVAC systems are typically comprised of fans and ductwork for moving air where needed. An HVAC system will include a cooling and heating section for, respectively, cooling and heating the air. In most HVAC systems, air is drawn in, filtered, cooled and dehumidified or heated and humidified, and then delivered to a room. The greatest portion of this air is drawn from the conditioned space for recirculation through the HVAC system. Considerable effort has been made to make these components more efficient.

One of several recently used methods of saving energy in an HVAC system includes the use of variable frequency drives on any motor used in a HVAC system. When and if the system load decreases, this can be sensed and the motors in the HVAC system will be slowed to an equilibrium value to save motor energy consumption. Another method is to reduce the design amount of outdoor air to eliminate having to condition it. Another method is an economizer cycle that utilizes 100% outdoor air when its ambient temperature is suitable for cooling the space. Another method is to replace aging equipment with newer and more efficient equipment.

One other factor impacting design and operation of HVAC systems is indoor air quality (IAQ). One major factor in IAQ today is the amount of outdoor air introduced into an otherwise sealed space serviced by an HVAC system. The HVAC industry has adapted standards for the introduction of outdoor air into spaces serviced by an otherwise closed HVAC system. These include offices, residential, commercial, industrial and institutional spaces, as well as the interior of vehicles such as cars, buses, planes and ships. In addition to controlling indoor air for occupant comfort, the goal of HVAC systems is to provide air with reduced levels of particulates, gases and bioaerosols, be it for semiconductor, pharmaceutical or food processing facilities, hospitals, schools or offices and now the home.

Most ventilation systems today include a cooling section. The cooling section includes a type of heat exchanger typically referred to as a "cooling coil," through which air is forced and cooled. This cooling coil operates thermodynamically to remove both sensible and latent heat from the forced air. Cooling coils typically are made using aluminum fins over refrigerant tubes which have been formed into a desired shape. Essentially the same coil arrangement in used in all cooling systems, whether in HVAC systems for occupied spaces, or for refrigerators and freezers.

A similar configuration is often used in heating sections, though the thermodynamic operation is opposite to that in a cooling section. The heat exchanger of a heating section often comprises a coil, and water of an elevated temperature passes through the coil. The heating coil is fashioned in a manner to promote heat transfer from the water to the heating coil. The heating coil is further fashioned to promote heat transfer from the heating coil to air which is forced across and through the heating coil.

As a normal consequence of the process of cooling air, several things occur. One is that humidity (latent heat) is removed from the air. This moisture collects on the coil fins and/or anything else nearby which is below dew point, including the ductwork. Typically, a drain pan is positioned below a cooling coil. The collected moisture runs down the fins and into the drain pan under the force of gravity. Water which collects in the drain pan flows away through a drain pipe equipped with a trap.

Another is that organic matter deposits and collects on the cooling coil fins from the air passing over them. Though the fins of the cooling coil appear to be smooth, in fact, when viewed under a microscope, they can be seen to have an irregular and somewhat pitted surface. The organic matter can therefore adhere easily to the damp and rough surface of the cooling coil.

Another consequence is that the cooling section is dark and at off times, it will be warm. Though when operating it will be quite cold, the cooling section will have varying cycles of cooling. When not cooling, the cooling coils typically reach room temperature.

Similar effects are encountered with heating coils, though typically to a lesser degree than with cooling coils.

Altogether, these consequences produce an environment in which molds and bacteria can grow and thrive. Over time, a heat exchanger can become near fully encrusted with microorganism activity bound to an organic substrate. The drain and drain pans also become a growth environment for mold and bacteria. The spores and products of metabolism from both are easily entrained into the airstream.

As this matter encrusts a heat exchanger, its heat exchange efficiency is compromised. The efficiency reduction does not result in an energy reduction. Instead, in the case of a cooling coil, the cooling coil must be made to be cooler or run longer, both of which require more energy for the same unit of work. In the case of a heating coil, the heating coil must be made to be hotter or run longer, both of which require more energy for the same unit of work. Furthermore, more energy is required to push air across the encrusted heat exchanger, resulting in an increased pressure drop. Therefore, either the fan speed must be increased, the motor horsepower increased, or both, or an oversized fan and motor are installed. Pressure drop and heat exchange efficiency can degrade up to 30% of their original values in as little as one year, on average 22% in three years. There is an exponential increase in energy consumption to the linear degradation of HVAC system heat exchange efficiency and airflow. A 30% degradation can equate to a doubling of energy use when these other remedial measures are used.

The conventional method of controlling the accumulation and growth of substrate and microorganisms is with the use of high-pressure sprayers, surfactants, acids and biocidal agents, which are applied to all growth surfaces of the HVAC system. However, the surfactants, acids and biocidal agents are dangerous chemicals and the distribution and use of biocidal agents and acids are strictly controlled by the Environmental Protection Agency (EPA). In this age of workplace safety, there is worry not only for the occupants of the building, but also for those working on the buildings mechanical equipment. Thus, those who supply and apply these materials must use masks, gloves and gowns when handling them. These chemicals are dangerous enough that the HVAC system must be shut down and the building vacated. As can be imagined, conventional treatment can be extremely expensive.

Despite the inconvenience and cost, treatment may only be effective for as little as three days to three weeks and usually not more than three months. Furthermore, chemical cleaning provides only a partial reduction of cooling coil pressure drop and a partial increase in heat exchange efficiency. To make matters worse, conventional cleaning techniques eventually damage the heat exchangers resulting in the entire heat exchanger or air handler being replaced—a very expensive event. Because of the problems with these chemicals, the continuous encrustation of heat exchangers has been largely ignored.

If done properly (i.e., regularly), the cleaning of heat exchangers can be very expensive. With cooling coils having as many as fourteen fins per inch and staggered refrigeration tubes every two inches of coil depth, cooling coils are rarely if ever cleaned completely, therefore ending in an eventual point of no return. The process is also destructive to the cooling coil, limiting the number of times the procedure can be performed. Speeding up the fan requires new sheaves and belts. Furthermore, this results in increased energy consumption, as brake horsepower increases to the cube of fan RPM.

$$\frac{HP_2}{HP_1} = \left(\frac{RPM_2}{RPM_1}\right)^3$$

Thus, increasing the fan motor size or replacing the fan and motor with larger ones only adds to the overall energy consumption.

In order to achieve minimum IAQ levels, other modifications are used. One is to introduce extra outdoor air. However, this leads to extra cooling, heating and filter costs, and may even exacerbate the heat exchanger encrustation.

Another method is to use "high efficiency particulate arrester" (HEPA) filters instead of standard particulate filters. The installation of HEPA filters, their support assemblies and maintenance is very costly. There are also very substantial indirect costs as more power from a fan is needed to push air through the denser HEPA filters, which follows the criteria indicated above.

The present invention arose from testing of UVC Emitters™ as manufactured by Steril-Aire U.S.A., Inc., the assignee hereof. The UVC Emitters are Steril-Aire's high output germicidal lamps, which are specifically designed for cold and moving air environments such as found in HVAC systems. In the test, UVC Emitters were installed within an air handling system owned by Southern California Air Conditioning Distributors, Inc. (SCACD), in City of Industry, Calif. Specifically, UVC Emitters were installed so that their ultraviolet light output in the C band (UVC) was directed toward the cooling coil of the air handling system. The tests were unconcerned with energy consumption. Rather, these tests were designed to measure improvements to IAQ derived from eradicating mold and bacteria using the UVC Emitters.

It was clear to SCACD that the cooling coil in its air handling system was becoming less and less efficient, so that the air handling system had to consume more energy to provide its function. The cooling coil of the air handling system at SCACD's City of Industry facility was approximately twenty years old. SCACD, the worlds largest privately owned distributor of air conditioning equipment, had been unable to prevent cooling coil encrustation in its own facility. SCACD had tried all conventional cleaning methods, which eventually provided little benefit. Thus, over time, the air handling system required increasing amounts of energy to produce the same net cooling effect. It was SCACD's expectation that the cooling coil or system would need to be replaced in order to obtain a reasonable flow of air of suitable temperature.

The testing of SCACD's cooling system was performed using scientific and industry procedures under the supervision of Dr. Robert Scheir, one of the assignors hereof and a respected Ph.D. in Medical Microbiology. Prior to installation of the UVC Emitters, measurements were taken by SCACD of the air pressure drop across the cooling coil and the air entering and leaving dry and wet bulb temperatures. The UVC Emitters were then installed and the cooling coil was exposed continuously to the UVC output of the UVC Emitters for four weeks. On Sep. 28, 1997, new measurements were taken of the air pressure drop across the cooling coil and the air entering and leaving dry and wet bulb temperatures. It was concluded that the heat exchange efficiency of the cooling coil had increased and the air pressure drop across the cooling coil had decreased. SCACD's cooling coil appeared to have returned, as much as possible, to an "as new" condition, something that was heretofore believed impossible by any method. Though the UVC Emitters were believed to have some contribution to the results of the test, SCACD officials and the inventors remained skeptical that the UVC Emitters could have been exclusively responsible for the results.

It was not until several weeks later, after additional testing and analysis, that the inventors hereof were able to confidently declare that the UVC Emitters were responsible for the decreased air pressure drop and increased efficiency of SCACD's cooling coil. Furthermore, from this work, the inventors were able to formulate and refine the particular configuration, mathematics and specifications by which energy usage would predictably be reduced in an air handling system using UVC irradiation.

The use of germicidal lamps for air sterilization only in ductwork, though once considered potentially viable, is no longer well known to those skilled in the art. Various reasons have contributed to the lack of success in utilizing germicidal lamps, except for limited and specialized purposes. The functional implementation of such devices in air moving systems has been limited generally to expensive portable units or top-of-the-wall or ceiling systems where the germicidal lamp is situated in a minimum air movement and ambient air temperature area. Germicidal lamps have sensitive physical characteristics, including plasma gases, mercury and partial pressures thereof When germicidal lamps are used to irradiate a moving air stream, the air moving across the germicidal tube lowers the tube's temperature. The mercury condenses such that the emission of the germicidal wavelength of 253.7 nm in a conventional tube decreases as much as a 75% when the temperature falls below 58° F. The phenomenon, referred to as skin-effect cooling, increases the number of conventional tubes, reduces the available square area for airflow, reduces air changes per hour, and increases the number of expensive tube replacements required to obtain an anticipated level of performance.

Germicidal lamps emit ultraviolet light at the primary and secondary emission lines of mercury (254 nm and 185 nm). At mercury's 185 nm line, ozone is created. Ozone has strict threshold limit values due to its strong oxidative properties and potential harm to humans. Despite the clear benefits of germicidal lamps, problems such as ozone, decreased output in low temperatures and moving air and the resulting short tube life have prevented their use in all but the most friendly of environments.

For further information concerning improvements in electrical discharge devices which are directed to overcoming such problems, reference is made to U.S. Pat. No. 5,334,347 entitled, "Electric Discharge Device" which is co-owned with this application, and a pending application filed in the name of two of the instant inventors, Forrest B. Fencl and Robert M. Culbert, entitled "Single-Ended Germicidal Lamp for HVAC Systems," application Ser. No. 08/773,463 the disclosures of which are incorporated herein by reference. Germicidal fixtures have recently become available under the Germ-O-Ray and Germitroll trademarks for installation in air ducts. The particular capabilities and design of these devices is not known to the inventors, though it is believed that both devices use conventional tubes having relatively short life and low output.

SUMMARY OF THE INVENTION

The previously described problems are solved in methods and apparatus of the invention wherein ultraviolet radiation is directed to the heat exchanger of an air handling system. The ultraviolet light kills, degrades and vaporizes the microorganisms and other organic material which naturally forms over time on a heat exchanger. As this matter is eliminated, the pressure drop is decreased (i.e., airflow is increased) and the heat exchange efficiency (capacity) is increased. In particular, there is no organic matter to impair heat transfer from a cooling or heating coil, and less energy is used by the HVAC system to move air as the restriction to airflow is reduced.

The invention has numerous benefits and advantages over the prior art. The primary benefit is that the invention can amount to significant energy savings in a cooling or heating system. UVC does not require lowering the cooling coil temperature or raising the heating temperature, thereby avoiding the consumption of a significant amount of energy. UVC does not require modifications to fan speed or motor horsepower, thereby further avoiding consumption of a significant amount of energy. Using standard life cycle analysis, UVC energy proves to be the least expensive method of cleaning an installed heat exchanger. UVC energy can also maximize the useful life of a heating exchanger rather than minimize it. UVC can return more coil surface and open area, heat, and thus transfer and airflow than any other method.

Still further objects and advantages will be apparent to those skilled in the art from the following particular description.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein.

These and additional embodiments of the invention may now be better understood by turning to the following detailed description wherein an illustrated embodiment is described.

DETAILED DESCRIPTION OF THE INVENTION

Throughout this description, the preferred embodiment and examples shown should be considered as exemplars, rather than limitations on the apparatus and methods of the present invention.

Figure 1:
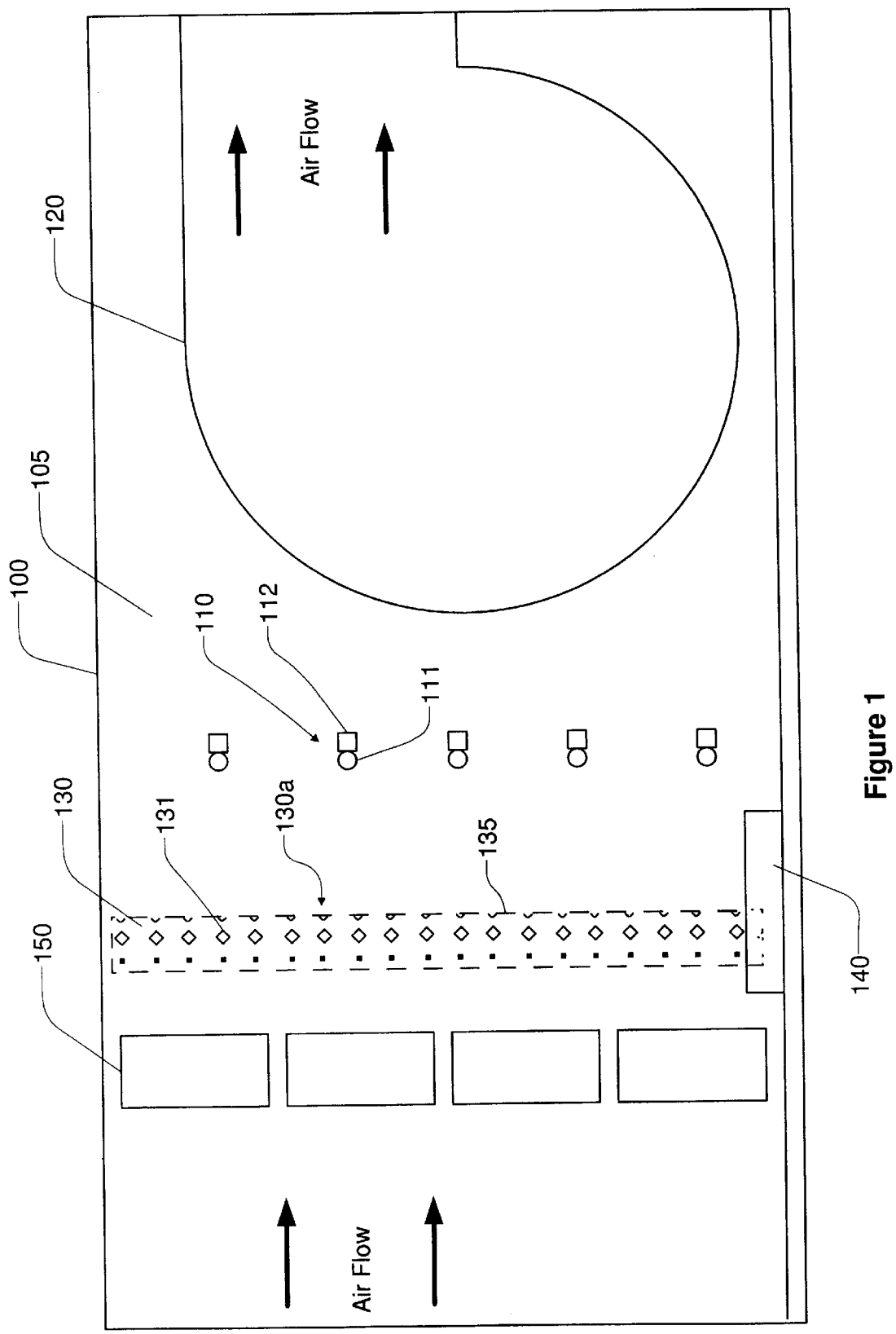
FIG. 1 is a diagrammatic side elevational view of a part of an HVAC system illustrating the positioning of a germicidal tube relative to a heat transfer coil and a drain pan.

Referring now to FIG. 1, there is shown an air duct or plenum 100 of an HVAC system, through which air is discharged in accordance with the operation of a suitable blower or fan 120. A number of germicidal lamps 110 are mounted in a chamber 105 of the air duct 100. The germicidal lamps 110 include a germicidal tube 111 coupled to and carried by a base 112. For the germicidal lamps to operate effectively in the harsh environs of an air duct, it is preferred that germicidal lamps specifically designed for such environments be employed. In particular, the germicidal lamps sold by the assignee of this invention, Steril-Air U.S.A., Inc, and sold under the trademark, "UVC Emitter," are preferred. The base 112 contains electrical circuitry and ballast for energizing the a germicidal tube 111 to emit ultraviolet radiation, preferably in the "C" band (UVC). Although not shown in FIG. 1, there may be a number of single-ended germicidal tubes coupled to a single base as shown in FIGS. 14–18, with the base mounted on the outside of the duct 100. Such a configuration is disclosed in the co-pending application referred to above, "Single-Ended Germicidal Lamp for HVAC Systems." Other configurations of germicidal tubes and bases are within the scope of the invention.

A horizontal flow, flat heat transfer coil 130 and drain pan 140 of the HVAC system are positioned within the chamber 105, preferably upstream from the germicidal lamp 110 with reference to the air flow. While this is the preferred positioning, it is to be understood that the lamp 110 may also be positioned upstream from the coil 130 and drain pan 140, whichever provides good uniform radiation coverage of the coil 130 and drain pan 140 and best accommodates the HVAC system's layout.

The coil 130, which is well known in the art, comprises circuited tubes 131 through which refrigerant circulates and a number of substantially flat, planar parallel fins 135 attached at generally regular spaces on the tubes 131. The relationship between the coil tubes 131 and the fins 135 can be better appreciated from FIG. 3. The fins 135 increase the effective surface area of the tubes 135 to thereby increase heat transfer from the air to the surface of the coil 130. Because of the excellent heat transfer properties, low expense and ease of manufacture of aluminum, a typical coil is substantially constructed of this material. In general, for heat transfer, cost and manufacturing reasons, the fins 135 are rarely coated. Coincidently, aluminum has in excess of 60% reflectivity for the primary UV emission line, a wavelength of 253.7 nm. However, the method of the invention is also applicable to fins of other materials which are relatively good reflectors of UV's primary emission line.

Further upstream from the coil 130 may be a number of filters 150.

Figure 2:
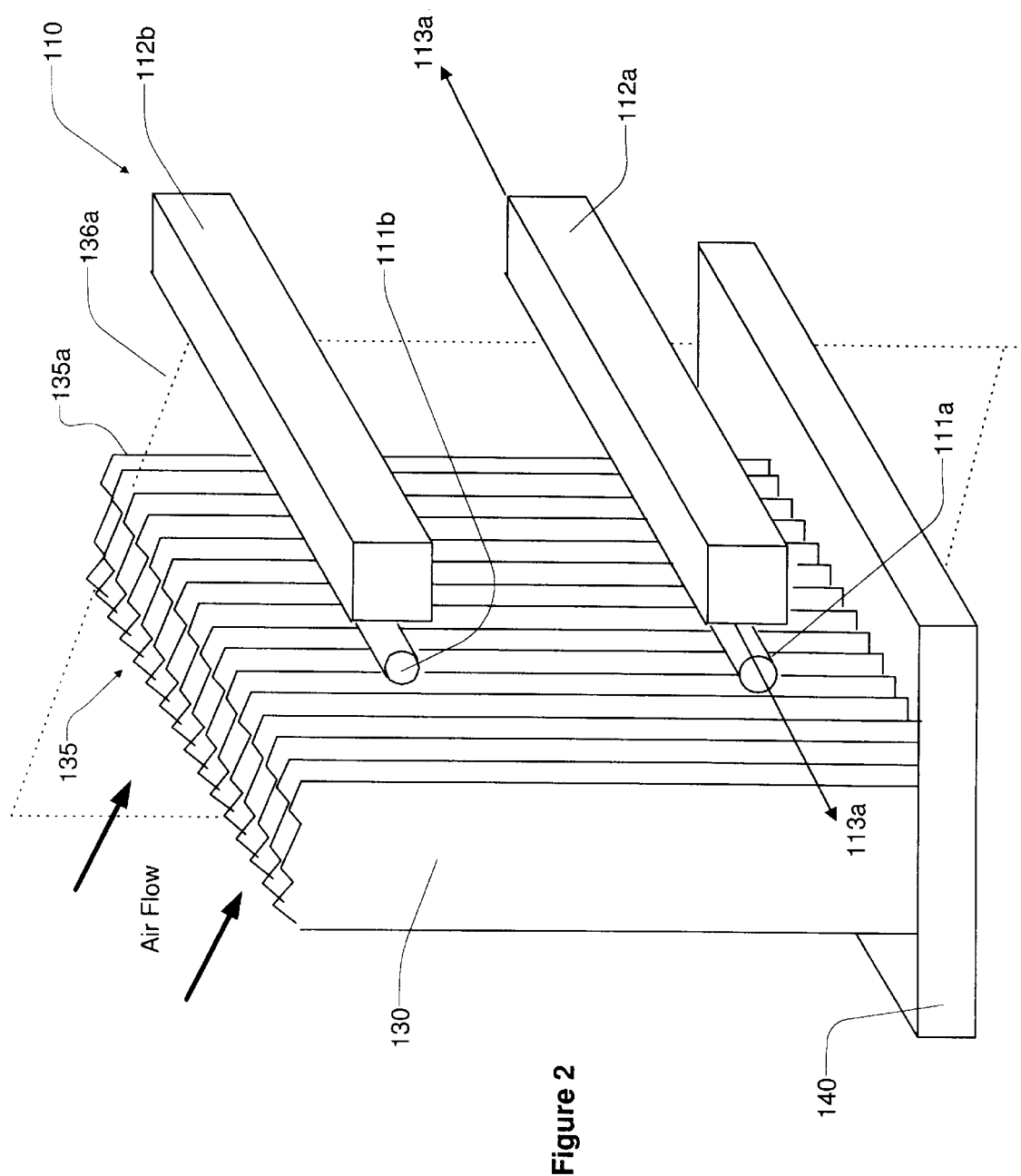
FIG. 2 is a diagrammatic isometric elevational view of a horizontal flow flat heat transfer coil to illustrate the positioning of germicidal tubes relative of the coil's heat transfer fins.

Referring now to FIG. 2, there is shown a diagrammatic perspective view of the fins 135 and the germicidal lamps 110. For a given fin 135a, there is defined a plane 136a of the fin 135a. For a given germicidal tube 111a, there is defined a longitudinal axis 113a. Preferably, the longitudinal axis 113a of the germicidal tube 111a is at a right angle to the plane 136a of the fins 135a. Since the fins 135 are parallel and vertical, the germicidal tubes 111 will be at right angles and horizontal to the plane of all of the fins 135.

Figure 3:
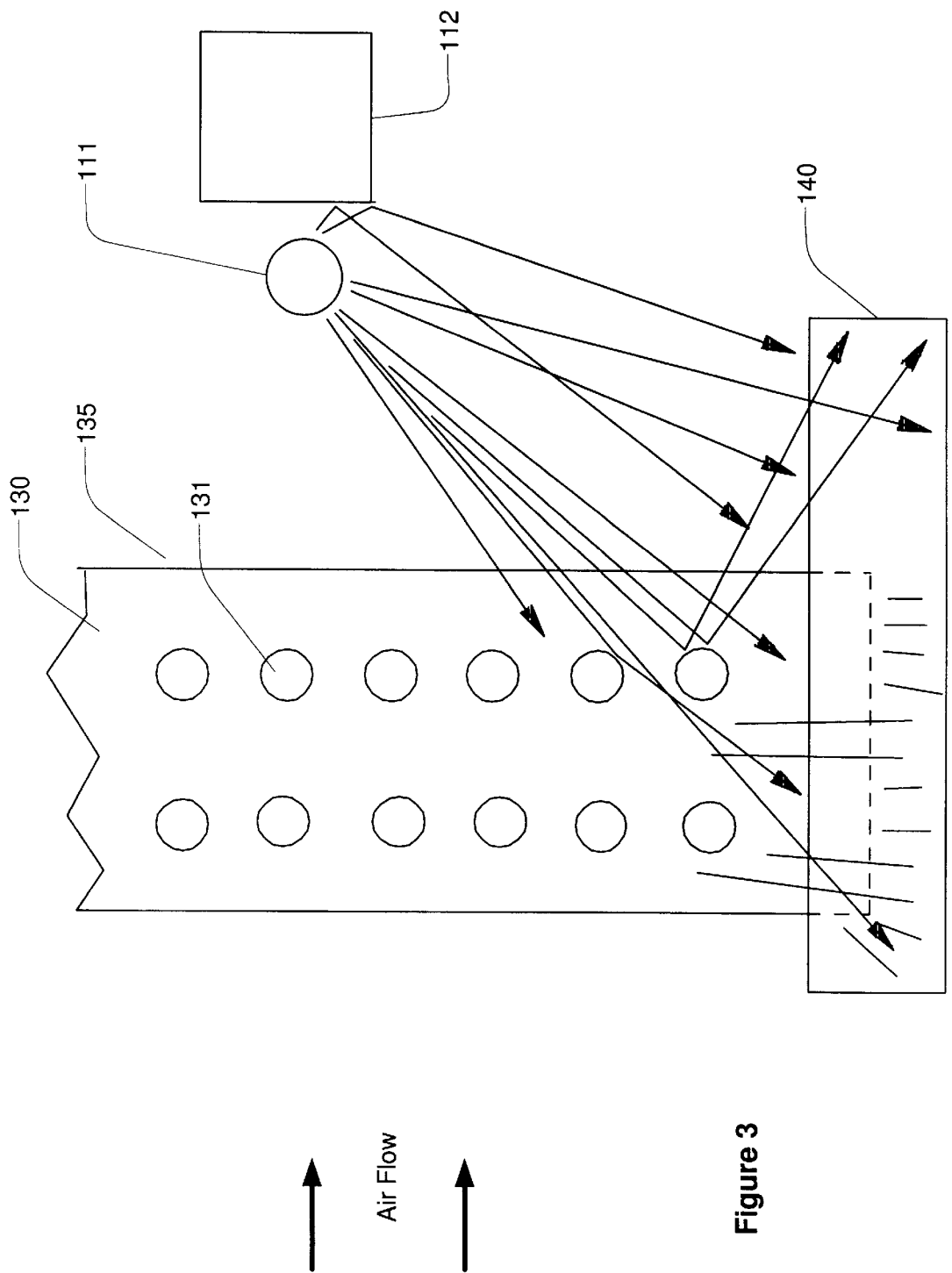
FIG. 3 is a diagrammatic elevational illustration of a portion of the cross section of the horizontal flow flat heat transfer coil illustrated in FIG. 2 to better illustrate the manner in which the germicidal tube is positioned adjacent to the coil and drain pan—perpendicular to the parallel planes of the coil and illustrating the manner in which UV irradiation is applied thereto.

Referring now to FIG. 3, it can be seen that at least one germicidal tube 111 is also positioned so as to irradiate at least part of the drain pan 140 directly. In accordance with the invention, the coil's tubes 131 and fins 135 reflect UV radiation from the germicidal tube 111. The fins 135 also reflect UV radiation on into the drain pan 140. Accordingly, the surface of the drain pain 140 will also be irradiated through reflections of the UV radiation from the tubes 131.

Figure 4:
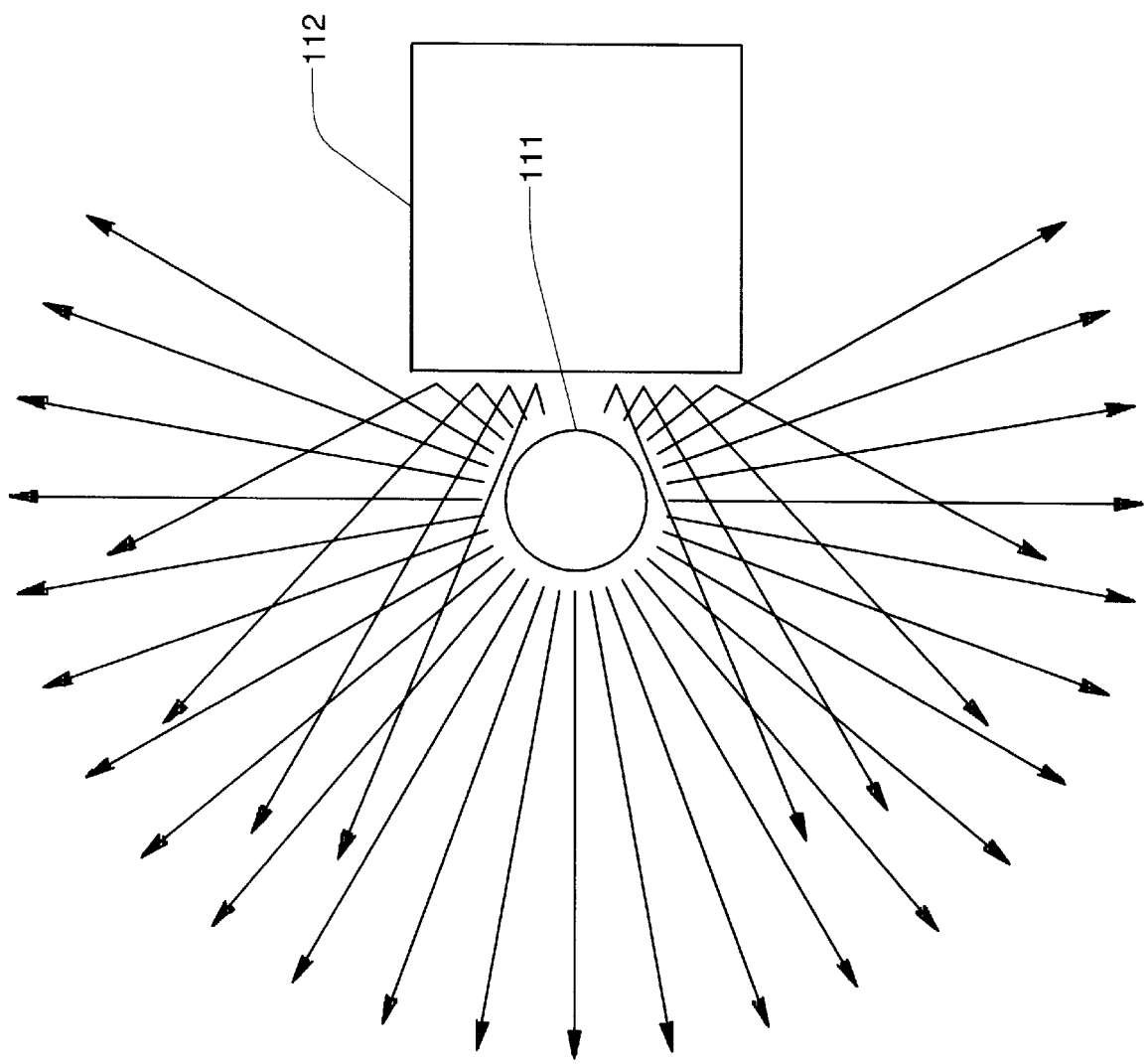
FIG. 4 is a diagrammatic side elevational representation of a germicidal fixture and tube taken in a plane perpendicular to the longitudinal axis of the germicidal tube and fixture to illustrate radiation emitted from the germicidal tube when in that plane.

In determining the spatial relationship between the germicidal tubes 111 and the coil 130 (FIG. 1), the objective is to obtain a uniform distribution of UV radiation across the coil's face 130a. (The coil's face 130a also substantially defines the leading edge of the coil's fins 135.) It has been determined that, for a germicidal tube which is positioned in accordance with the invention, the spatial distribution of UV radiation follows precisely that of a diffuse area source and, surprisingly, not an isotropic point source. The pattern of UV radiation from a germicidal lamp is shown in FIG. 4. It can be seen that although the germicidal tube 111 is a source of radiation, the base 112 is effectively a secondary (reflected) source of UV radiation. The diffuse radiation of the germicidal tubes 111 and diffuse reflection is therefore defined as a near field effect, not as an inverse square law. This finding is contrary to normal expectations, and therefore placement of germicidal tubes in accordance with the present invention results in the need for fewer germicidal tubes. Put another way, when the germicidal tubes 111 are positioned in sufficient proximity to the coil 130, the intensity of UV radiation from the germicidal tubes 111 striking the coil 130 is, to a degree, independent of the distance of the germicidal tubes 111 from the coil 130.

In one embodiment of the invention, germicidal tubes, spaced 24 inches apart, were positioned at right angles to the plane of the fins and about twelve inches from the drain pan and twenty inches from the face of the coil. It has been found that positioning the germicidal tubes 111 20 inches from the leading edge 130a of the fins 135, in conjunction with appropriate germicidal tube-to-tube spacing, is particularly effective in inhibiting the growth of microorganisms on all surfaces of the coil 130 and in all surface areas of the drain pan 140.

As shown in FIG. 4 the photons emitted from a particular point on the germicidal tube 111 radiate in all directions. Because FIG. 4 is an elevational view, the global radiation of these photons is not shown. These photons would, however, also radiate outwardly and inwardly from the plane of the paper upon which the planar representation is illustrated and from all surfaces of the tube 111. In addition, to increase the photons applied to the coil and drain pan, a germicidal lamp with a reflector (preferably incorporated in the base 112) is utilized. Those photons emitted and reflected in a plane parallel to the planes of the fins 135 penetrate into the coil 130 and are reflected by the internal coil structure (i.e., the tube 131 and the fins 135).

Figure 5:
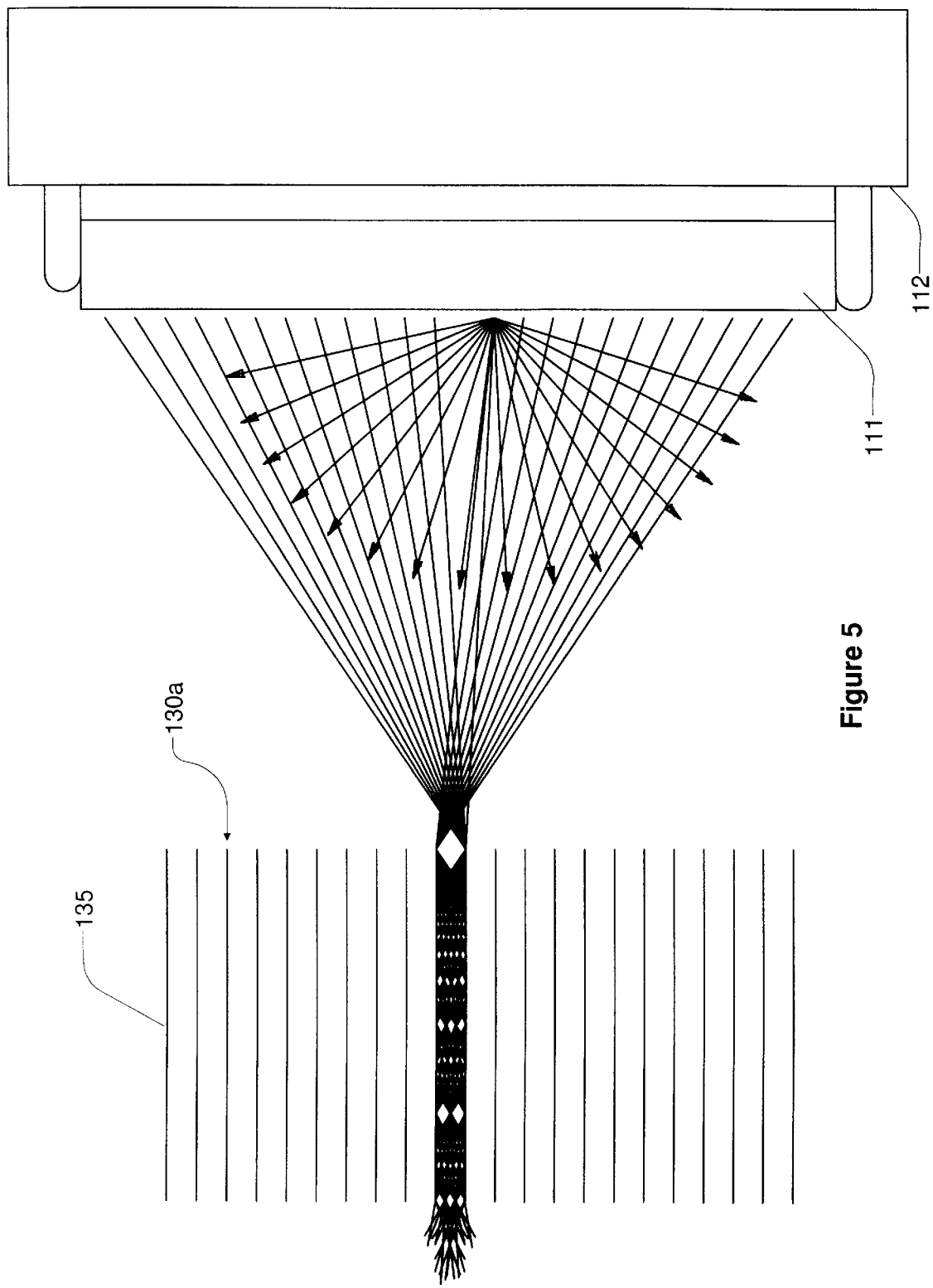
FIG. 5 is a diagrammatic planar representation of UV radiation emitted from the germicidal tube illustrated in FIG. 4 taken in a plane parallel to the longitudinal axis of the lamp and perpendicular to parallel planes of the heat transfer fins to illustrate the directing and reflecting of UV irradiation from all points of the lamp in that plane when applied between adjacent vertical planes of the heat transfer fins, and the manner in which a particular point on the tube will radiate photons in the direction of the fins and reflecting off the fins to increase flux density and dosage applied thereto.
Figure 6:
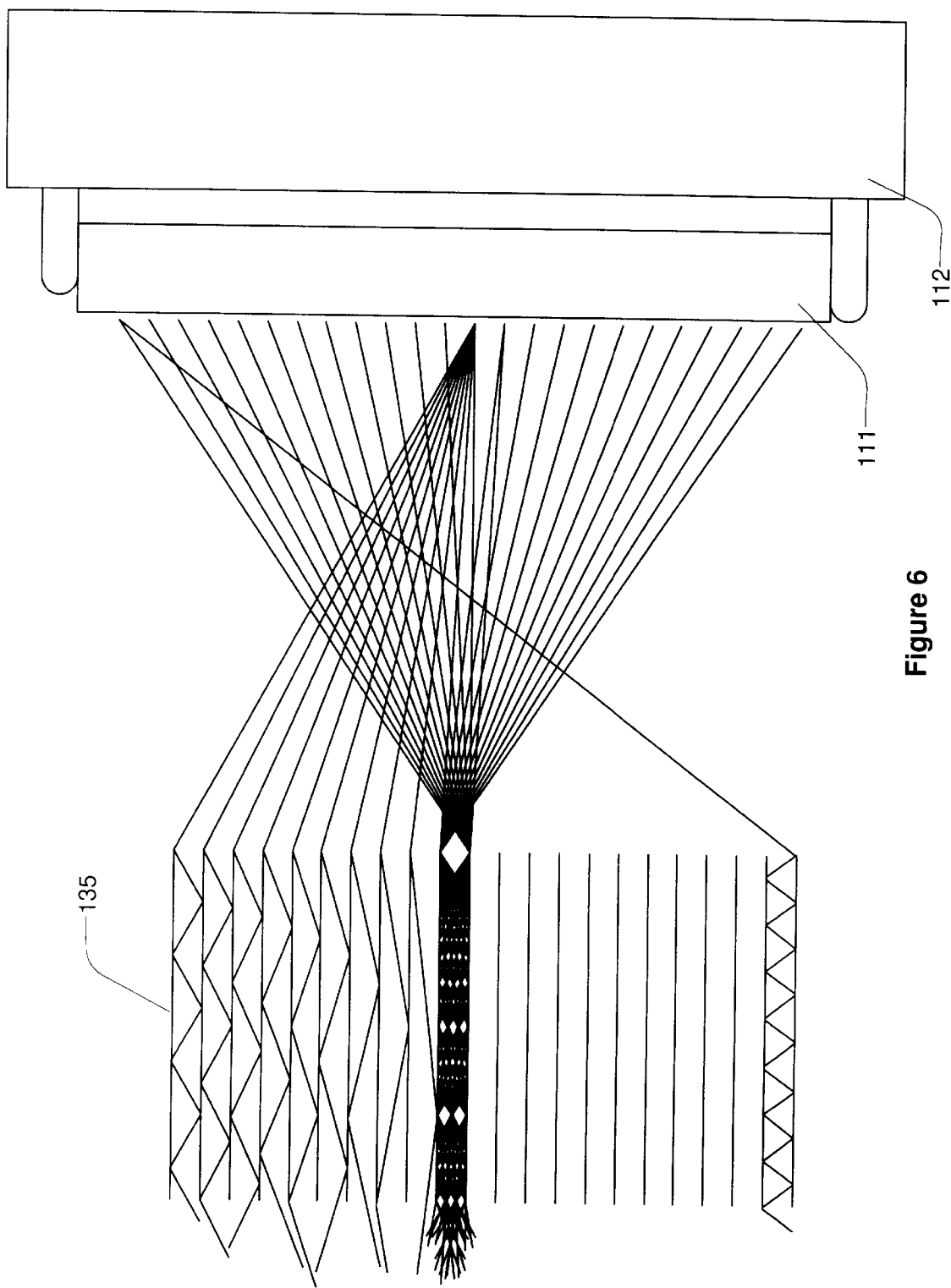
FIG. 6 is a diagrammatic planar representation as in FIG. 5 illustrating the manner in which the UV radiation from all points of the germicidal tube in that plane will be applied between each pair of adjacent parallel planes of the fins, and the manner in which the radiation from a particular point on the germicidal tube will be received and reflected between all of the parallel fins of the coil's tubes for a better understanding of how the radiated energy and subsequent irradiance of that energy is accumulated and thus enhanced.

As illustrated in FIGS. 5 and 6, because of the global emission of photons from the germicidal tube 111, photons emitted from all points on the germicidal tube 111 and reflected from the base 112, other than those emitted in a plane parallel to the planes of the fins 135 strike the fins 135 adjacent to their leading edge 130a (the edge closest to the germicidal tube 111) are reflected between the spaced parallel fins 135 in accordance to the angle of incidence that the photon takes. The fins 135 and circuited tubes 131 therefore reflect photons amongst one another such that the photons are applied throughout the coil 130 and the drain pan 140. Because the global emission occurs from all points along the longitudinal axis 113a of the germicidal tube 111, the flux density and uniformity of incidence to the fins 135, the circuited tube 131 and the drain pan 140 increases in the manner diagrammatically illustrated by the reflectivity shown occurring between a pair of fins 135 in each of these Figures. Such increased flux density and dosage occurs between all of the spaced parallel fins 135 and drain pan 140 in this manner. However, for purposes of illustration, such increases are shown in FIG. 5 occurring between only two adjacent fins.

As can be seen from these Figures, complete and uniform irradiation is achieved. Preferably, the number and position of germicidal tubes is selected so that the UV radiation is uniformly distributed across the coil 130 and drain pan 140.

Figure 7:
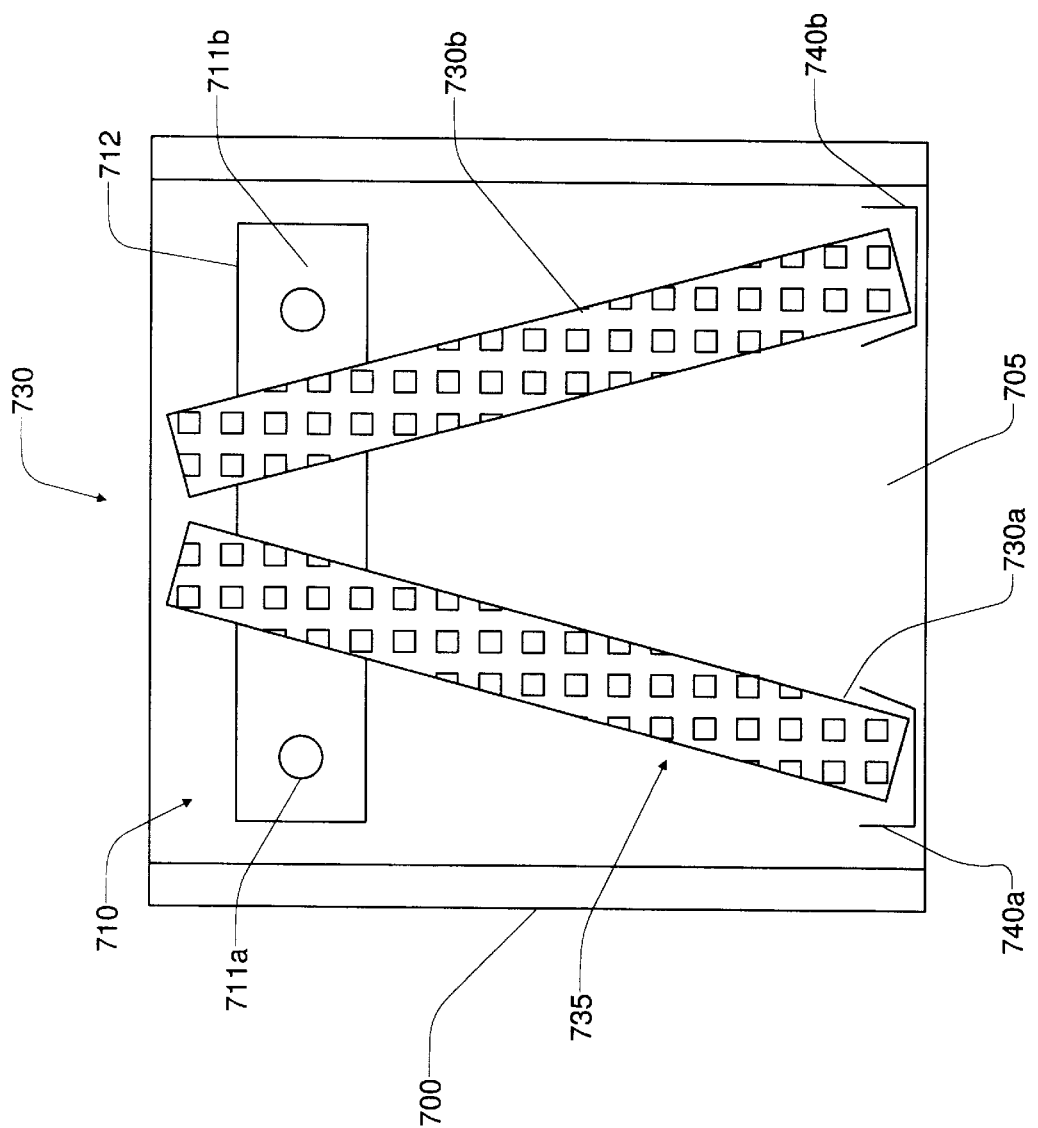
FIG. 7 is a diagrammatic illustration of the cross section of a residential "A" coil to illustrate positioning of a germicidal tube perpendicular to the coil's fins in accordance with one aspect of the invention.
Figure 14:
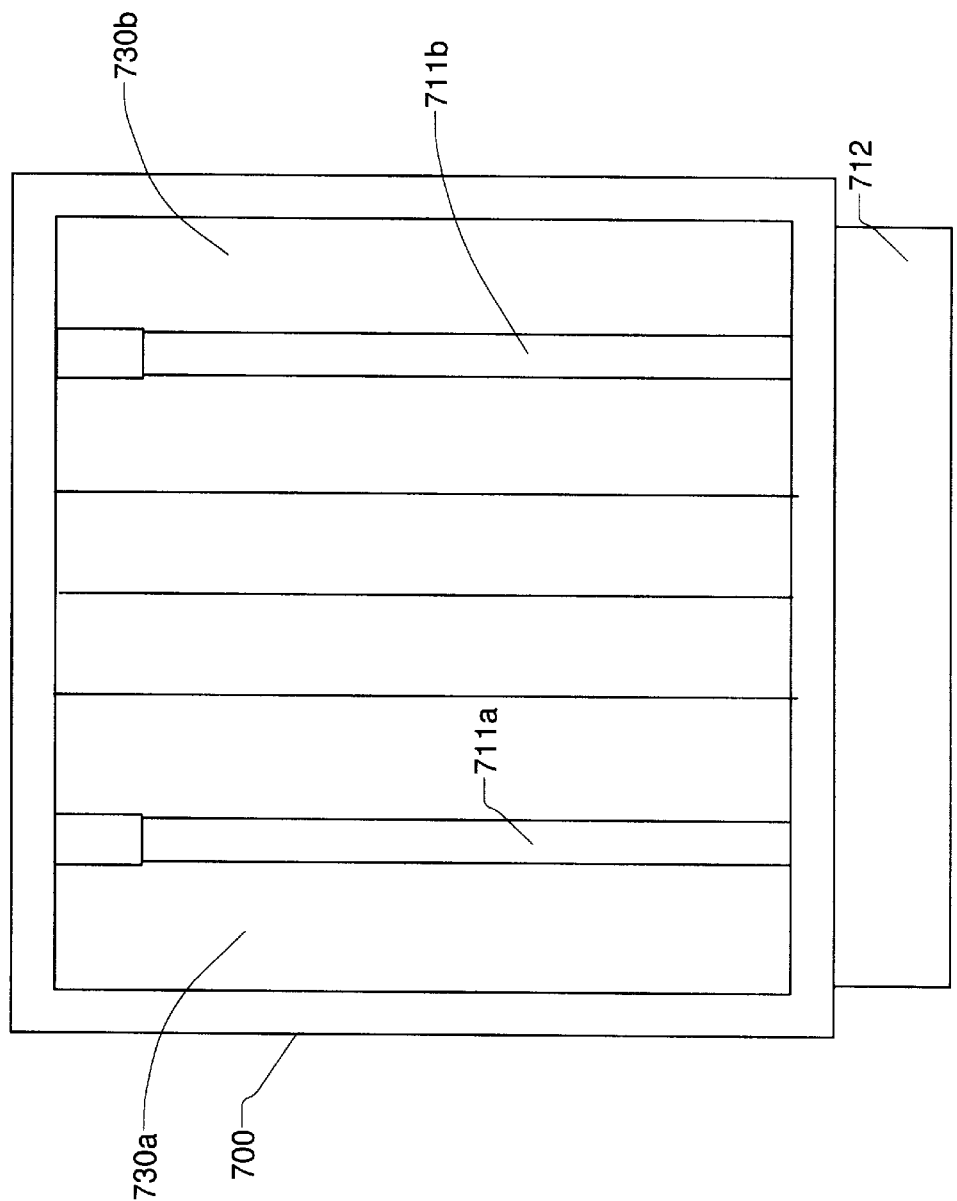
FIG. 14 is a planar top view of the residential "A" coil showing the germicidal tubes as perpendicular to the plane of the coil's fins.

Referring now to FIG. 7, there is shown a diagrammatic illustration of the cross section of a vertical flow "A type" heat transfer coil 740 to illustrate positioning of germicidal tubes 711a, 711b perpendicular to the coil's fins in accordance with one aspect of the invention. The germicidal tubes 711a, 711b, in base 712, are positioned at right angles to the planes in which the fins 735 lie. The germicidal tubes 711a, 711b will also partially directly irradiate the drain pans 740a, 740b, while the coil 730 will cause direct and indirect (reflected) irradiation of the drain pans 740a, 740b in the manner described above. FIG. 14 is a partial top view of the A coil and germicidal tube of FIG. 7.

It has been determined that positioning the germicidal tubes such that their longitudinal axes are perpendicular to the parallel planes in which the fins extend causes the emitted UV radiation to be applied directly and indirectly to the heat transfer coil and surrounding areas in the path of emission and reflection, and on into the drain pan. The actual positioning of the germicidal tubes, and the number of germicidal tubes to be employed in order to attain these objectives, is determined based on the goal that the UV radiation is uniformly distributed across the coil and drain pan.

Because the UV radiation strikes the fins and circuited tubes at all incident angles, they continuously reflect and effectively direct the UV radiation within and throughout the coil. This continuous reflection and direction of the UV radiation increases the flux density of the photons applied to the coil, the drain pan and continues in the airstream until absorbed. The increased number (flux density) of incident photons also assures that organisms in the airstream are struck from all angles. Also, the increased distance of photon travel, and thus available time of exposure, provides for a potentially greater dosage (intensity multiplied by time) to be received by any surface or airborne microorganism. In this manner the coil, drain pan and surrounding area are completely exposed to the UV radiation sufficiently to eradicate surface and substantially reduce airborne microorganisms.

Our continued research into the positioning and aiming of germicidal lamps and into various target environments for germicidal lamps has enhanced our understanding of them. For example, we have learned that the greatest "time weighted" amount of nutrient and moisture is in the cooling coil and not the drain pan. Because of this, the most active region of microbial activity (number) in an air conditioning system is in the cooling coil and during and after the cooling cycle. This conflicts with our initial deduction that the drain pan, when the air conditioner is not running, is the most active region.

As we focused on the cooling coil, we learned that in order to provide a complete kill throughout the cooling coil, a uniform distribution of germicidal UVC energy must be provided. This conflicts with our initial deduction that there must be a uniform amount of energy throughout the cooling coil. This difference resulted in the inventions claimed in our U.S. Pat. No. 5,817,276. In order to exploit the need for uniform distribution of energy, we have focused on positioning our UVC Emitters to maximize distribution of energy across a heat exchanger and throughout a heat transfer coil by reflection within the heat transfer coil. Our research has shown that while a higher output germicidal lamp is important, unexpectedly good results are achieved by aiming and reflecting the UVC radiation to maximize uniform distribution (irradiation).

Our initial focus was on IAQ. Thus, we expected that the best location for a germicidal lamp is downstream of a cooling coil, working from the highest degree of microbial activity to the lowest. As discussed above, to maximize uniform distribution of the UVC energy, the plane of the tube should be at a right angle to the conforming lines of the cooling coil's fins. Through initial radiation and incident reflection—total irradiation—UVC energy bathes all surfaces of the cooling coil and drain pan as well as the line-of-sight airstream.

In order to provide a uniform distribution of photon energy through the deepest part of a heat transfer coil, depending on its height and width, we prefer having several tubes at selected "tube to tube" distances and at selected "tube to coil" distances. The minimum photon energy striking the leading edge of all heat transfer coil fins is preferably 716 $\mu W/cm^2$ at the closest point and through placement, not less than 60% of that value at the farthest point. This therefore sets the minimum number of tubes, their center lines and their distance from the air-leaving or air-entering surface of the heat transfer coil. If positioned in this manner, nearly equal amounts of energy will also strike the drain pan in most cooling systems, either directly or indirectly. The particular position of a germicidal lamp relative to a heat transfer coil depends on the capabilities and characteristics of the germicidal lamp used.

Microbial samplings of several experimental sites showed a uniform kill of all microbial activity throughout the tested cooling coils. The killing of mold and bacteria on the cooling coils also reduced or eliminated microorganisms and their products from the airstream with reduction of the following products in the relevant occupied spaces:

Airborne primary solvents and volatile organic compounds.

Microorganism metabolic gas exchange, raising airborne $CO_2$, etc.

Spore production which causes forms of Sick Building Syndrome (SBS).

Particle toxins which can cause both SBS and Building Related Illness (BRI).

Other bioaerosol related IAQ problems such as allergy, asthma, and symptoms such as headache, burning eyes and fatigue.

Another important discovery from our recent research is that microorganism nutrients are primarily organic in nature. As these minute organic substances impinge on the surfaces of a heat exchanger, both mold and bacteria bind-up this material to the surface of the heat exchanger during their growth and division process to hold moisture and maintain activity. This results in the dingy, dirty appearance which heat exchangers obtain over time.

Our research has shown that the ionizing radiation from our UVC Emitters is a key element in the killing and degradation process of microorganisms in cooling and heating systems. An ion is a particle formed when a neutral atom or group of atoms gains or loses one or more electrons. An atom that loses an electron forms a positively charged ion, called a cation and an atom that gains an electron forms a negatively charged ion, called an anion. Our scientific testing has established that the dead microorganisms then further undergo damage through this free radical process. Absorption of UVC energy leads to the formation of radical cations, anions and electrons, and electronically excited molecules. One reason is that about 70% of the energy is absorbed by the available moisture and about 30% by organic matter and other solutes. Water absorption of UVC leads to the formation of oxygen/hydrogen radicals or hydroxyls, solvated electrons and hydrogen atoms which are all very safe to humans and the environment. This process is similar to that produced by outdoor sunshine. In these processes, the atoms are separated, thus disassociating individual whole molecules to produce individual radicals to the original structure. These water-derived radicals are all highly reactive and atomically degrade (vaporize) organic material.

Only after continued study did we learn that the degradation process continues on the dead microorganisms as well as any residual organic nutrients. In time, the heat transfer coil and drain pan become organically clean. We have observed this effect on severely encrusted cooling coils in as little as four weeks of continuous operation. The results from the UVC energy degrading the organic matter are:

Heat exchanger pressure drop goes back to "as new."

Heat exchanger airflow goes back to "as built" or "as installed."

Heat exchanger cleanliness goes back to "as built" or "as installed."

Heat exchanger capacity goes back to "as built" or "as installed."

Heat exchanger cleaning is no longer required.

Space humidity and temperature are more easily controlled.

Heat exchangers no longer seed the ductwork or space with bioaerosols.

The elimination of organic material from the heat exchanger as shown above has other significant advantages for the user from an energy standpoint. The reduction in pressure drop across the heat exchanger equates to a reduction in air horsepower and is expressed by the following formula:

$$Hp = \frac{CFM \times 5.2 \times \Delta PD}{33000 \, \eta}$$

Where:

Hp=horsepower

Figure 10:
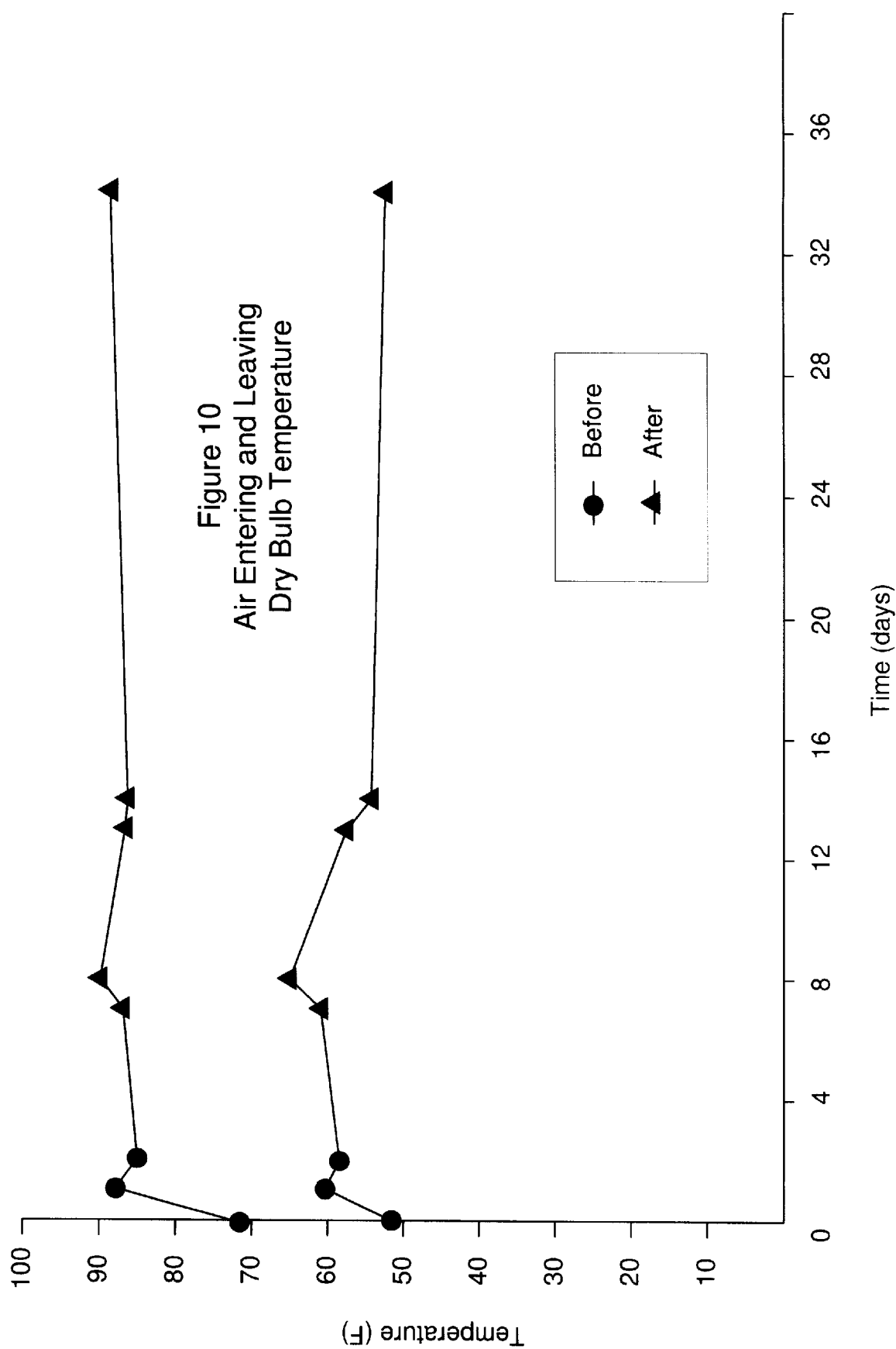
FIG. 10 is a graph of the air entering and leaving dry bulb temperature over several weeks during testing of germicidal lamps at SCACD.
Figure 11:
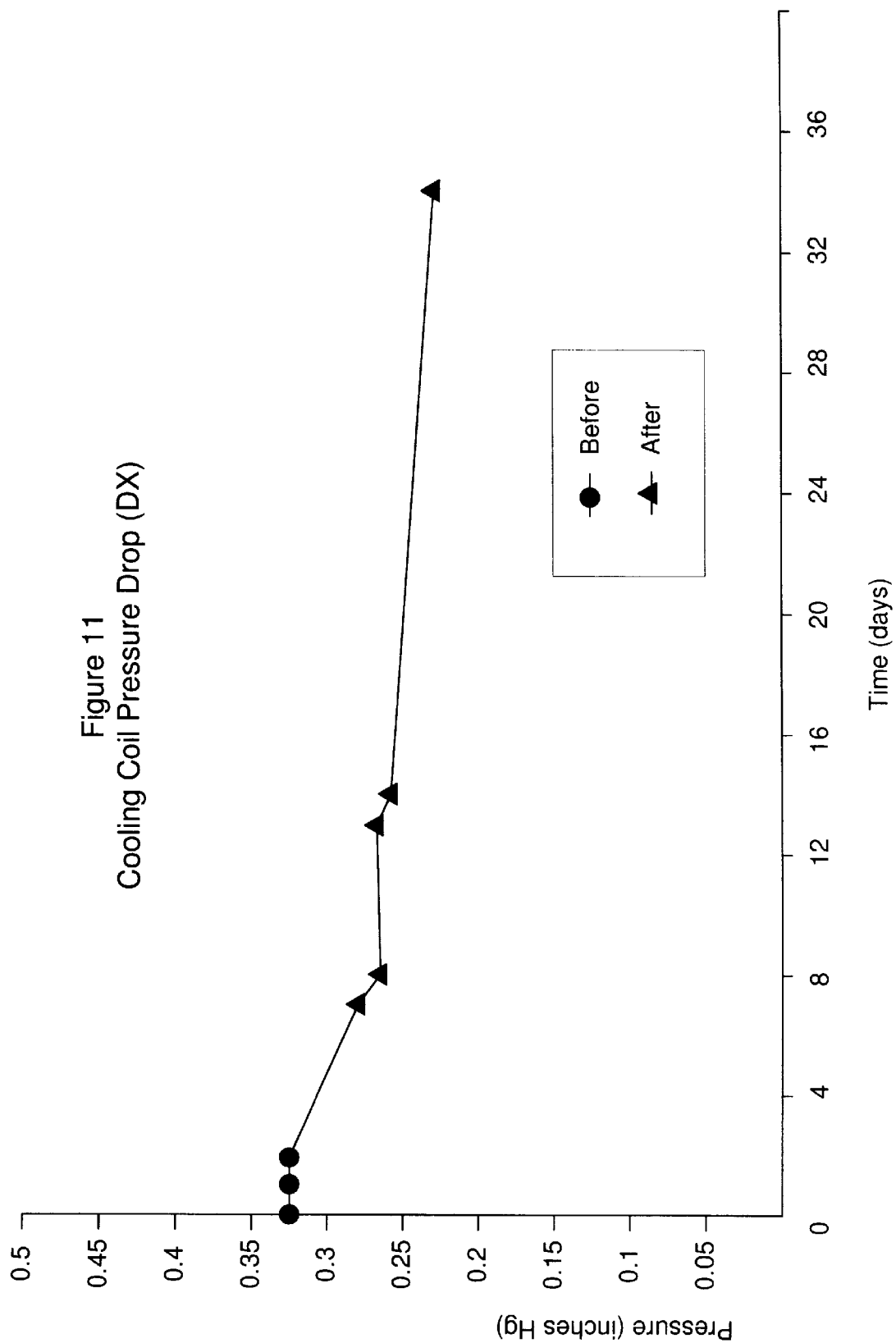
FIG. 11 is a graph of the air entering and leaving wet bulb temperature over several weeks during testing of germicidal lamps at SCACD.
Figure 12:
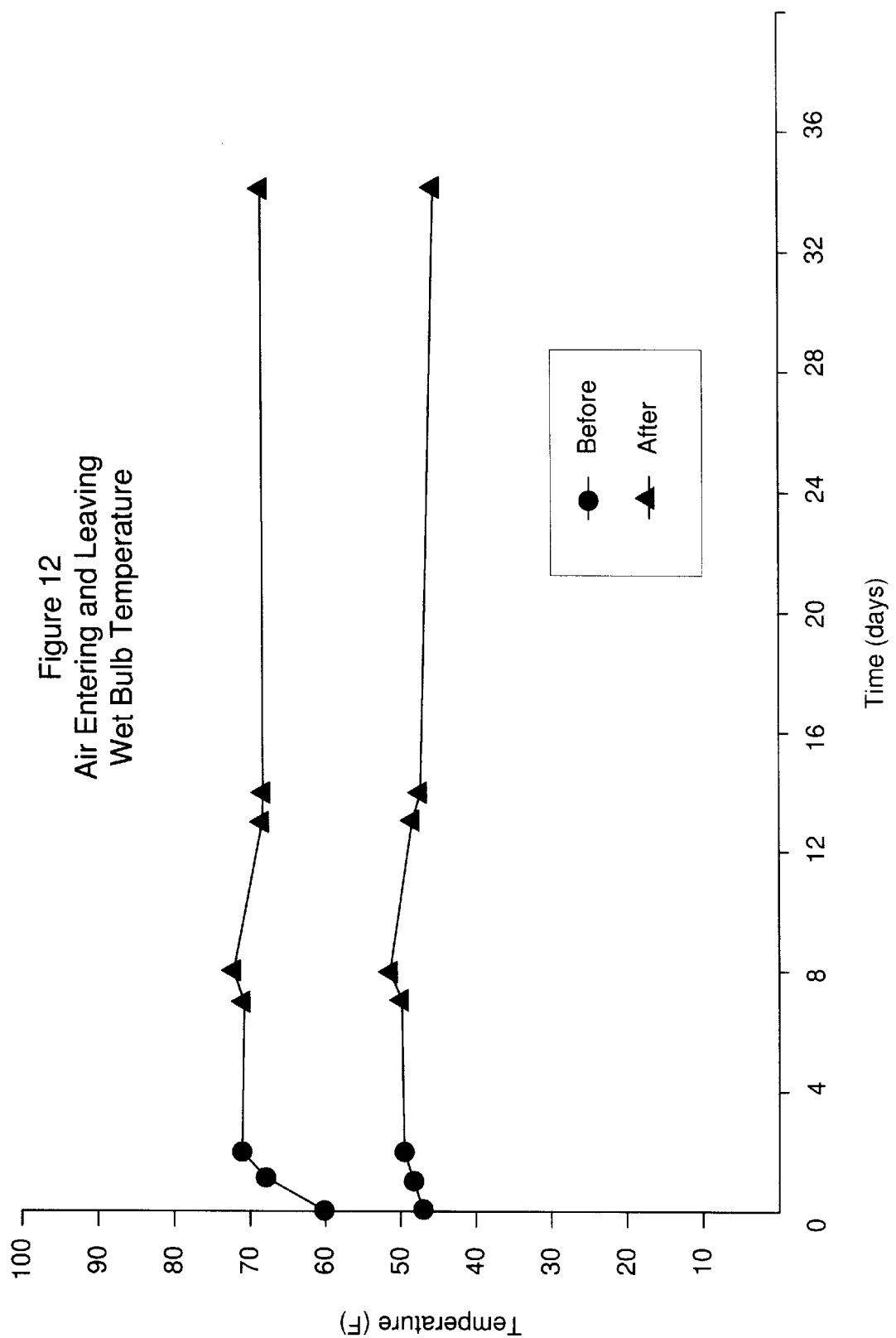
FIG. 12 is a graph of decrease in pressure drop over several weeks during testing of germicidal lamps at SCACD.
Figure 13:
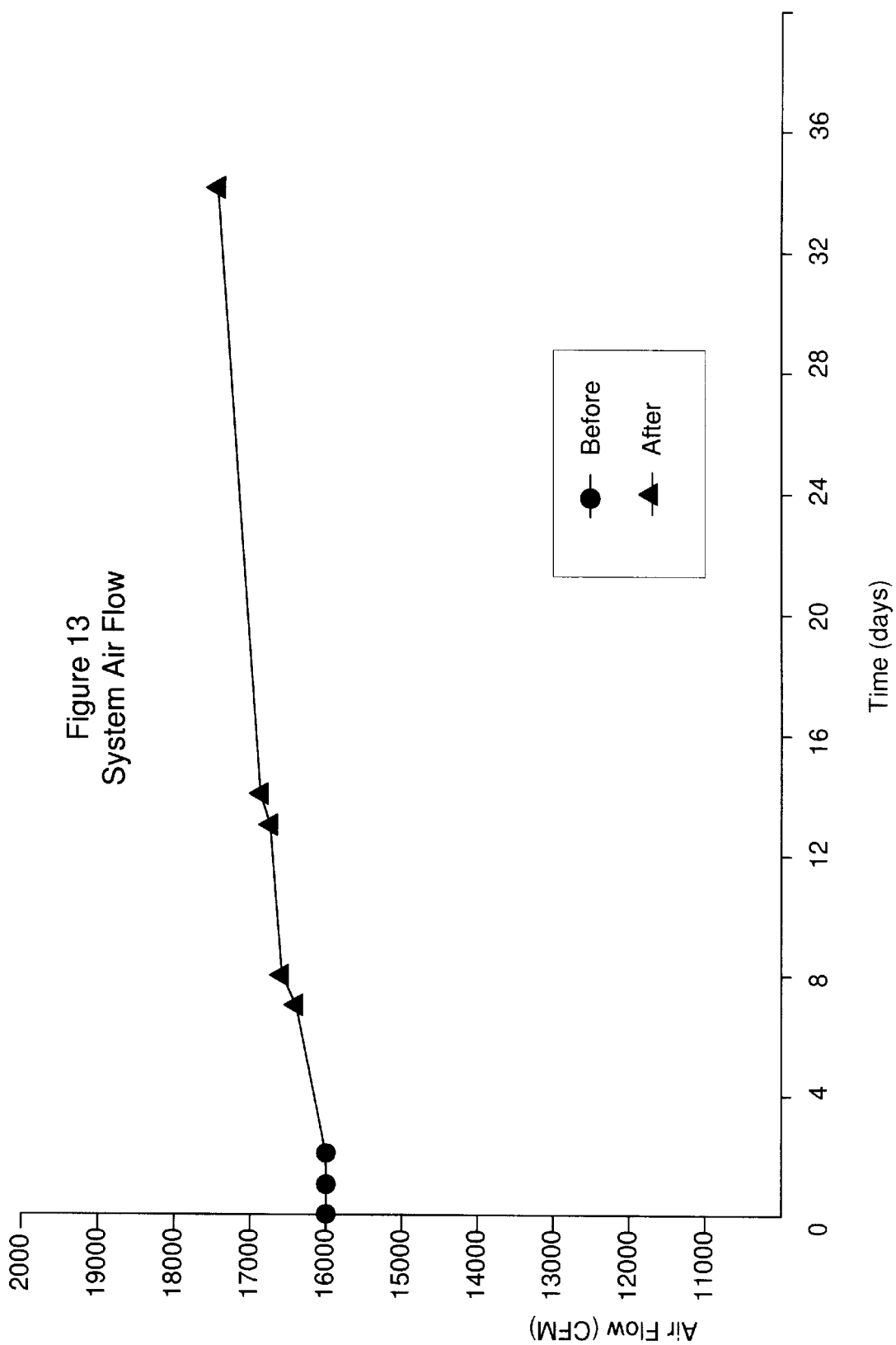
FIG. 13 is a graph of the increase in system CFM over several weeks during testing of germicidal lamps at SCACD.

CFM=cubic feet per minute 5.2=conversion of inches WG to psi $\Delta$PD=change in pressure drop across the heat exchanger 33000=conversion of foot pounds to horsepower $\eta$=system efficiency FIGS. 10, 11, 12 and 13 show graphs of "before" and "after" conditions at our test site at SCACD, discussed above. FIG. 10 shows the air entering dry bulb temperature and air leaving dry bulb temperature over a one month period. We found a 3.7° greater temperature differential after installation of the UVC Emitters. FIG. 11 shows measured cooling coil pressure drop over the same one month period. We found a 28% lower pressure drop across the cooling coil after installation of the UVC Emitters. FIG. 12 shows the air entering wet bulb temperature and air leaving wet bulb temperature over the one month period. We found a 1.8° greater temperature differential after installation of the UVC Emitters. FIG. 13 shows measured system air flow over the one month period. We found an 8.6% increase in system CFM after installation of the UVC Emitters.

Applying the reduction in pressure drop shown results in horsepower savings of 0.58 and when taken against the operating hours and the cost per kW, energy savings of approximately $163 per year are realized. However, the big savings are in heat transfer as shown in the Entering Air Temperature (EAT) and Leaving Air Temperature (LAT) of both the Web Bulb (FIG. 12) and Dry Bulb (FIG. 10). The resulting change in total heat exchanger capacity is expressed as:

Total Heat=4.5×CFM×($h_1$-$h_2$)

Where:

4.5=conversion of pounds of air to 1 CFM

CFM=cubic feet per minute $h_1$=temperature of air entering wet bulb $h_2$=temperature of air leaving wet bulb Applying the reduction in wet bulb LAT against the above formula, operating hours and cost per kW, energy savings of approximately $11,724 per year are realized. The impact nationwide of using UVC in this manner would be dramatic to say the least.

When germicidal tubes are utilized as described herein, total flux density between each of the fins of a heat transfer coil is at its highest. As such, microorganisms that are not defused to the heat exchanger's surface and killed are mostly killed in the air due to the increased flux density from the resulting irradiation and lack of shadows. This reduces (kills) airborne microorganisms by as much as 90% on a single pass, reducing the incidence of airborne transmitted infections including such diseases as measles, chicken pox, whooping cough, common colds, influenza and tuberculosis.

Our research shows that UVC energy at 253.7 nm ionizes the organic bonds (as described above) of the typical materials deposited on heat exchangers. UVC energy vaporizes these materials at the solid, molecular and atomic level. The process time averages about three weeks of continuous exposure to complete and then maintains the cleanliness of a heat exchanger for the life of the system. This in turn returns airflow to "as designed" values. The process has been confirmed repeatedly.

Figure 8:
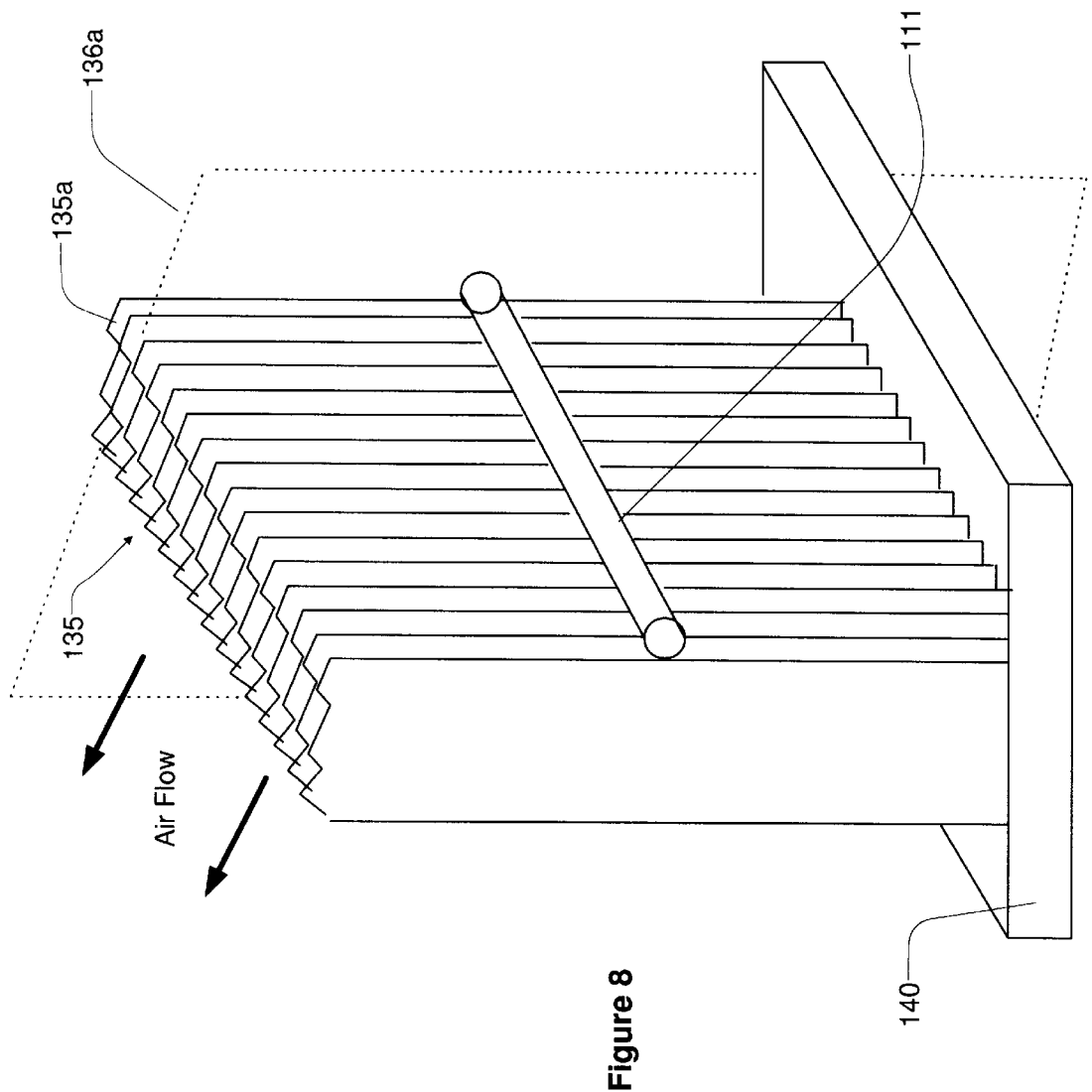
FIG. 8 is another diagrammatic perspective elevational view of a horizontal flow flat heat transfer coil to illustrate the positioning of germicidal tubes at right angles to the coil's heat transfer fins.

The process of cleaning the heat exchanger somewhat differs from the process of controlling the presence of surface and airborne microorganisms. The goal in cleaning the heat exchanger is to eliminate organic matter from all surfaces of the heat exchanger. In contrast, the goal in controlling the presence of surface and airborne microorganisms is to sufficiently kill just those microorganisms which are likely to affect IAQ. Thus, to maximize energy savings by eliminating organic matter on a heat exchanger, it may be necessary to locate germicidal lamps upstream from the heat exchanger as shown in FIG. 8.

Heat transfer coils are typically constructed of aluminum. Aluminum can reflect the 253.7 nm wavelength of UVC at up to 83%. Under a microscope and to the quarter micron wavelength of UVC energy, a heat exchanger's aluminum surface shows imperfections that look like peaks, valleys, pits and rocks. Installing our UVC Emitters at right angles to the plane of a heat transfer coil's fins results in the entire heat transfer coil surface receiving radiation through direct and/or incident angle reflection.

In accordance with the invention, UVC energy at 253.7 nm is utilized to vaporize accumulated debris reducing pressure drop and increasing heat exchange efficiency to "as new." The UVC light can be utilized upstream or downstream of the heat exchanger, whichever facilitates air handler design. Preferably, as described above, a tube's longitude is at right angles to the plane of a coil's fins. Preferably, tubes are positioned on center lines and distances from the top and bottom of the heat transfer coil to provide a uniform distribution of energy sufficient to clean the entire heat transfer coil surface through direct and reflected UVC energy.

The tubes of our UVC Emitters are preferably positioned from the heat exchanger surface at a distance which is equal to 80% of the distance of the light string centerline. For example, if the centerlines were 24", then the distance from the coil should be approximately 20". Preferably, the fixtures include a reflector to concentrate the energy produced, and the reflector is aimed toward the heat exchanger.

Once installed, the germicidal lamps are preferably run 24 hours per day until the heat exchanger is completely cleaned. Once the heat exchanger is cleaned, the germicidal lamps may be run intermittently as required to maintain the cleanliness and pressure drop of the heat exchanger.

Figure 9:
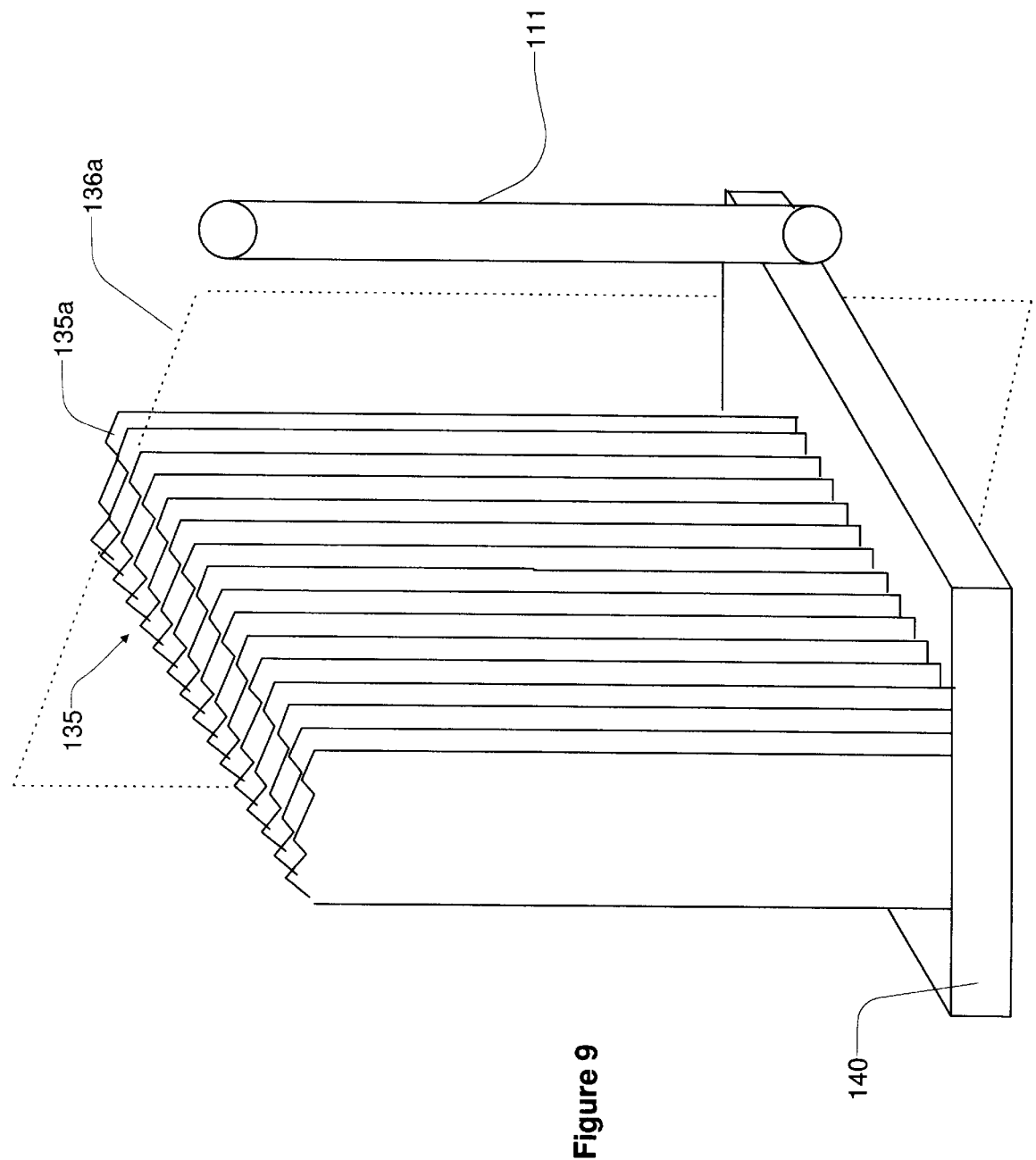
FIG. 9 is another diagrammatic perspective elevational view of a horizontal flow flat heat transfer coil to illustrate the positioning of germicidal tubes parallel to the coil's heat transfer fins.

For new heat transfer coils, germicidal lamps may be installed on the same plane as the plane of the fins, as shown in FIG. 9. The reason is that when the coil is new, the only requirement is to maintain it in the "as new" condition. This will save significant energy over the life of the system. While the amount of UVC energy reaching all surfaces of the heat transfer coil is less than in the preferred right angle position, calculations can be made that provide a degradation rate equal to the deposition rate of debris. This will keep the heat transfer coil clean indefinitely, which is the most affordable way to minimize energy use in exchanging heat or flowing air. These savings are shown in the formulas set forth above.

Figure 15:
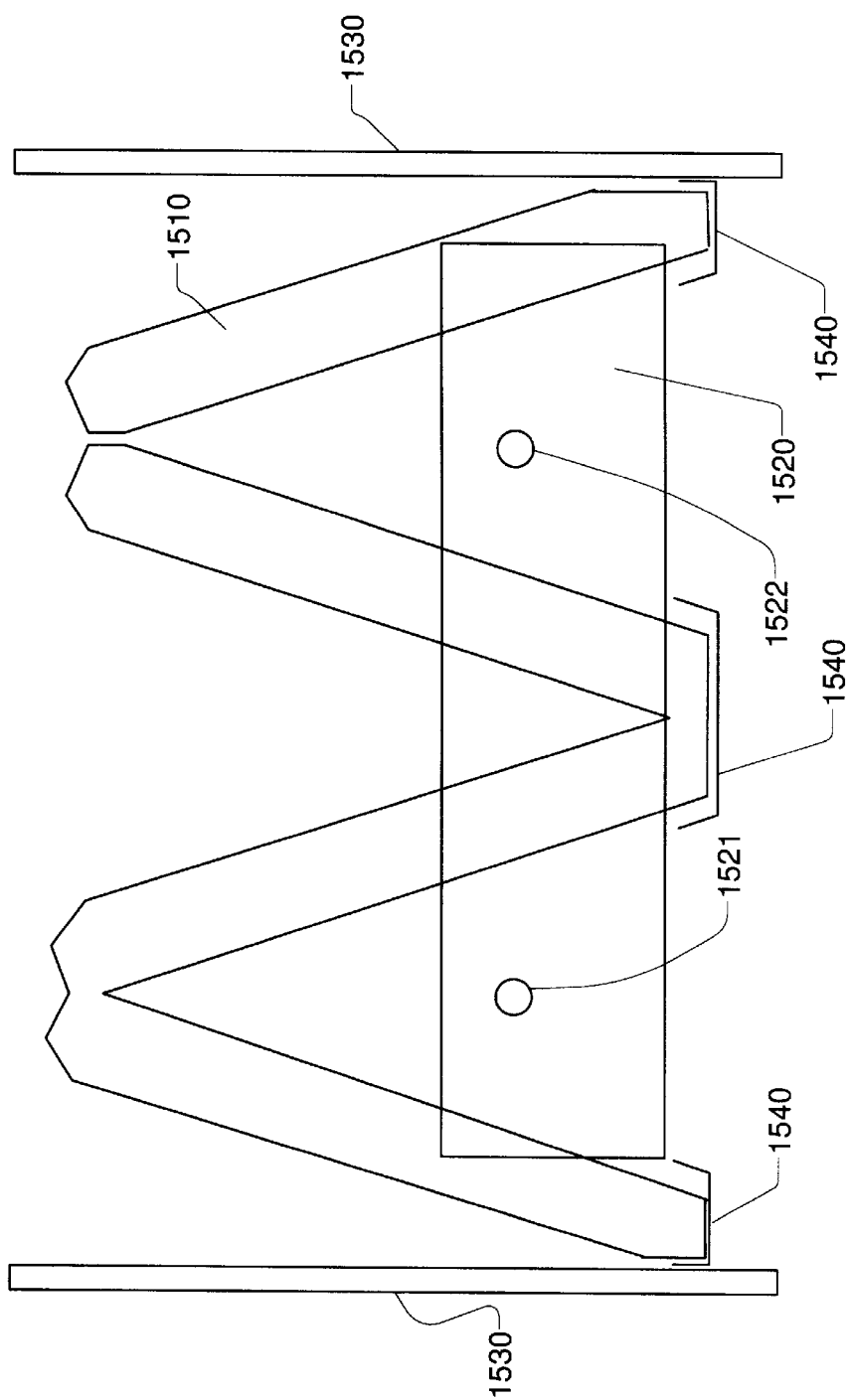
FIG. 15 is a diagrammatic illustration of the cross section of an "M" coil to illustrate positioning of a germicidal tube at right angles relative to the coil's fins in accordance with one aspect of the invention.
Figure 16:
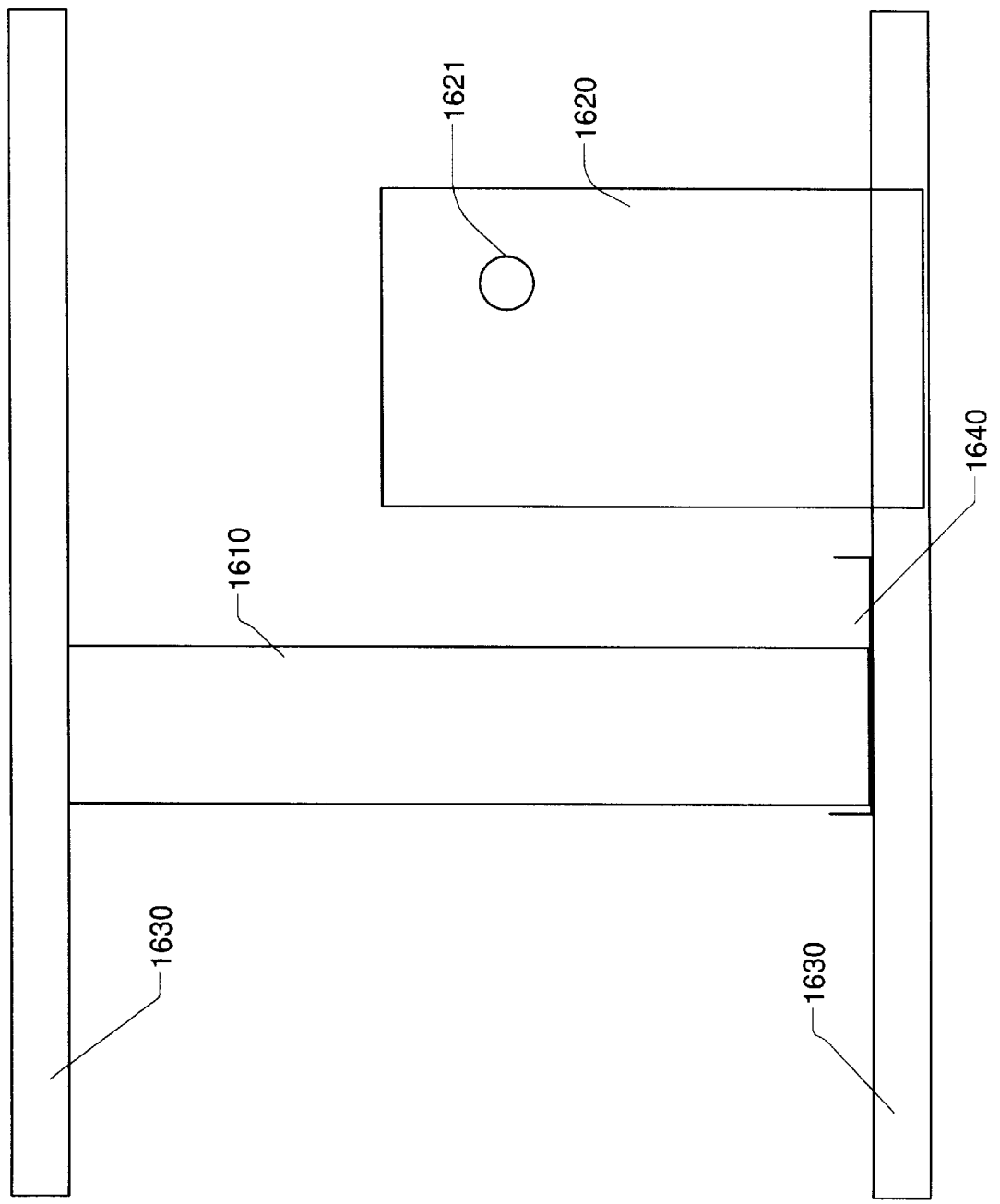
FIG. 16 is a diagrammatic illustration of the cross section of a single coil to illustrate positioning of a germicidal fixture relative to the coil in accordance with one aspect of the invention.
Figure 17:
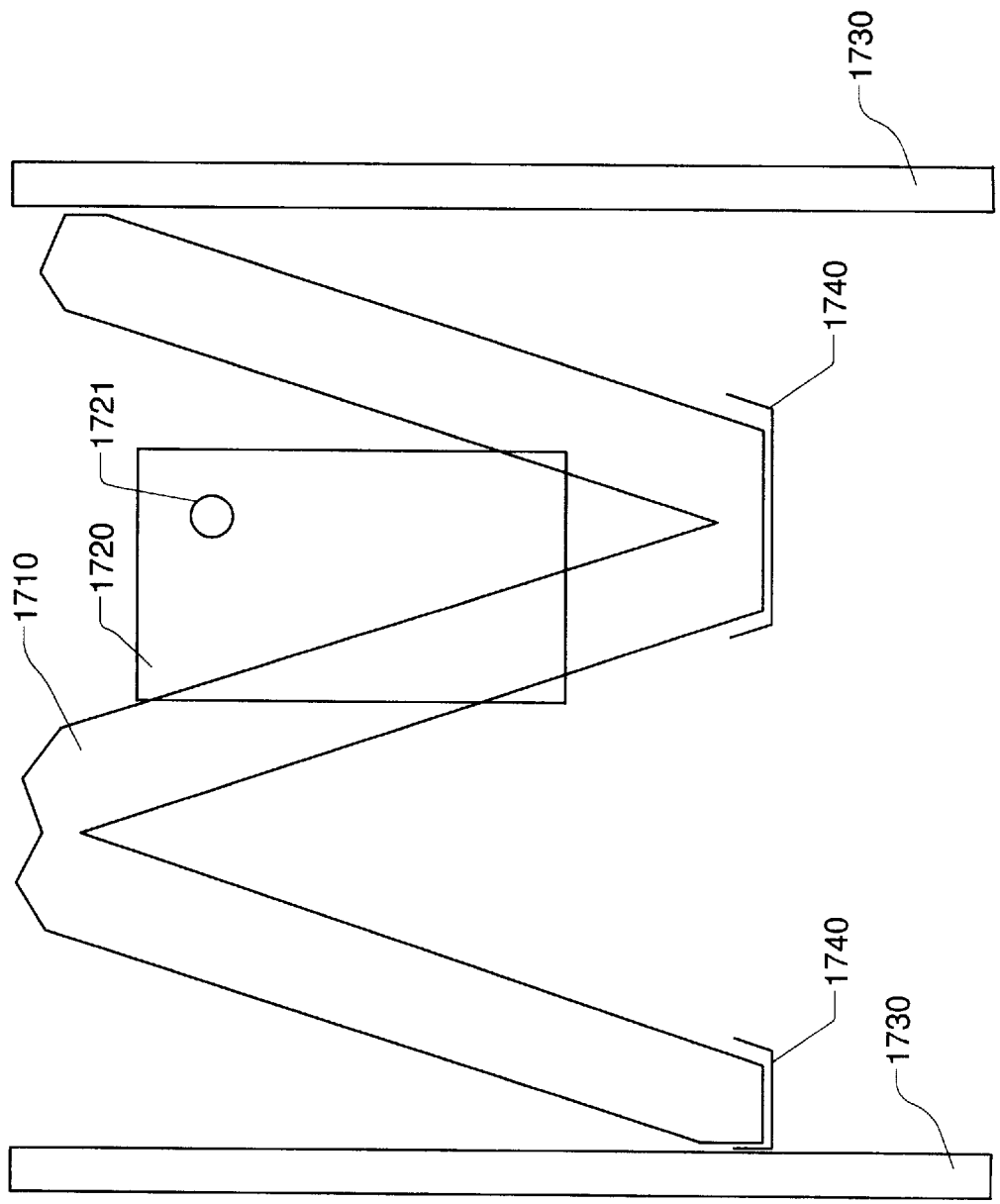
FIG. 17 is a diagrammatic illustration of the cross section of an "N" coil to illustrate positioning of a germicidal tube relative to the coil in accordance with one aspect of the invention.
Figure 18:
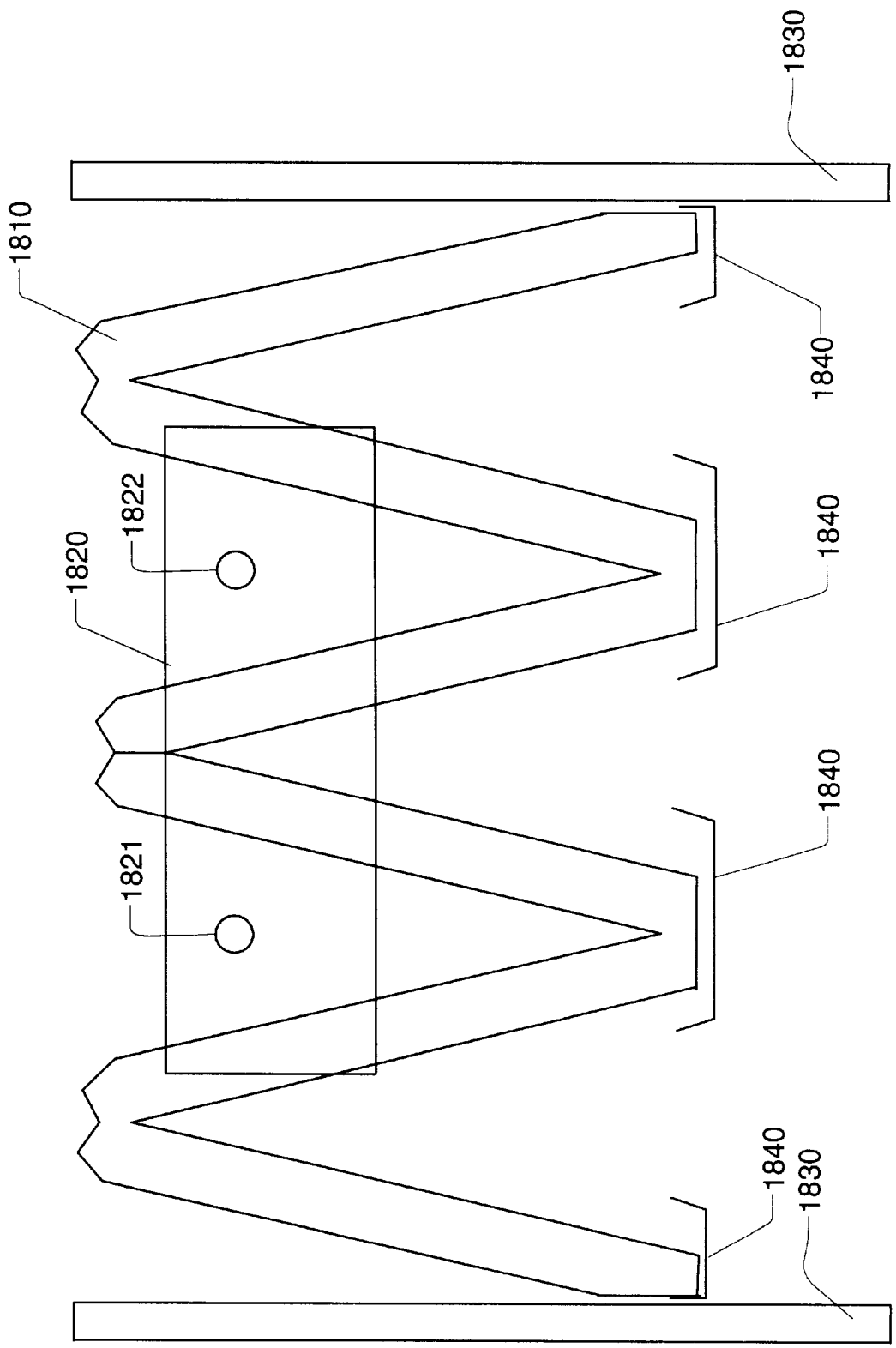
FIG. 18 is a diagrammatic illustration of the cross section of a complex coil arrangement to illustrate positioning of a germicidal tube relative to the coil in accordance with one aspect of the invention.

FIGS. 15–18 show various installations of germicidal lamps with respect to a variety of heat exchanger types. The installations of FIGS. 15–18 were achieved by considering both the desirability of reducing energy consumption, cost of installing a germicidal lamp (including the cost of the lamp itself), and structural limitations of the heat exchanger and its environs. FIG. 15 shows an "M" coil 1510, a dual-tube germicidal lamp 1520 including single-ended tubes 1521, 1522, insulated duct walls 1530 and drain pans 1540. FIG. 16 shows a slab coil heat exchanger 1610, a germicidal lamp 1620 including single-ended tube 1621, insulated duct walls 1630 and a drain pan 1640. FIG. 17 shows an "N" coil 1710, a germicidal lamp 1720 including single-ended tube 1721, insulated duct walls 1730 and a drain pan 1740. FIG. 18 shows a complex coil 1810, a germicidal lamp 1820 including single-ended tubes 1821, 1822, insulated duct walls 1830 and drain pans 1840.

Properly designed HVAC-type germicidal devices, such as our UVC Emitters, can be installed without interruption of the normal operation of an HVAC system. Because of the proven energy-saving abilities of germicidal lamps, other more expensive and less beneficial energy-saving devices may not be needed.

Once the germicidal lamps are installed and turned on:
Coil contaminants are ionized and degraded (vaporized).
The germicidal lamps clean the coil to "as new" specifications, completely returning heat exchange efficiency (heat removal) and pressure drop (airflow) to original values.
The germicidal lamps keep the heat exchanger in this condition for the life of the system.
The process is not destructive to the heat exchanger's surface or any other inorganic material.
The process requires no hazardous chemicals.
The process is environmentally friendly, as it adds nothing to the air or drainage system.
The germicidal lamps do the job continuously without shutting down the system or vacating the building.
A complete installation of germicidal lamps can cost less than a properly performed heat transfer coil cleaning.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

What is claimed is:

1. A method of reducing energy consumption in a heat transfer system through UVC irradiation, the heat transfer system comprising a heat exchanger having a surface, wherein the heat transfer system has an energy consumption level associated with an "as new" condition, and wherein during the operation of the heat transfer system, organic matter accumulates upon the surface of the heat exchanger, the accumulated organic matter thereby degrading the performance of the heat transfer system and resulting in an energy consumption level elevated above that associated with the "as new" condition, the method comprising the steps of:
    positioning and orienting a germicidal tube so that a minimum UV irradiance level on any point on the entire surface is sufficient to vaporize and remove organic matter on the surface when the germicidal tube is energized;
    energizing the germicidal tube to emit sufficient distributed UV radiation to vaporize and remove organic matter on the surface;
    maintaining energization of the germicidal tube until the accumulated organic matter deposited on the surface is substantially vaporized and removed; and
    operating the heat transfer system, energizing the germicidal tube to emit sufficient UV radiation to substantially vaporize and remove organic matter that accumulates during operation of the heat transfer system;
    wherein the wavelength of the UV radiation is 253.7 nm and the minimum photon energy striking the surface is 716 mW/cm$^2$ at the closest point of placement to the germicidal tube and not less than 430 mW/cm$^2$ at the farthest point from the germicidal tube;
    whereby energy consumption of the heat transfer system is maintained substantially at the energy consumption level associated with the "as new" condition.

2. The method of reducing energy consumption in a heat transfer system through UVC irradiation of claim 1, the heat exchanger comprising a heat transfer coil including a plurality of spaced fins, wherein the fins are parallel to one another, the method further comprising
    aligning the longitudinal axis of the germicidal tube in a position substantially perpendicular to the parallel planes of the fins; and
    reflecting and directing the UV radiation by the fins, thereby increasing the distribution and flux density of the UV radiation and the dosage of the radiation applied to the accumulated organic matter.

3. The method of reducing energy consumption in a heat transfer system through UVC irradiation of claim 2 wherein the reflecting and directing of the UV radiation received by the heat transfer coil is effected by the reflectivity of UV radiation from the materials from which the heat transfer coil is fabricated, thereby increasing the flux density of the radiation.

4. The method of reducing energy consumption in a heat transfer system through UVC irradiation of claim 1 wherein the heat exchanger reflects and distributes UV radiation around the heat exchanger to thereby increase the dosage of radiation applied to surfaces of the heat exchanger.

5. The method of reducing energy consumption in a heat transfer system through UVC irradiation of claim 1 wherein the heat transfer system comprises a cooling system.

6. The method of reducing energy consumption in a heat transfer system through UVC irradiation of claim 1 wherein the heat exchanger comprises a cooling coil.

7. A method of reducing energy consumption in a heat transfer system through UVC irradiation, the heat transfer system comprising a heat exchanger having a surface, wherein the heat transfer system has an energy consumption level associated with an "as new" condition, and wherein during the operation of the heat transfer system organic matter accumulates upon the surface of the heat exchanger, the accumulated organic matter thereby degrading the performance of the heat transfer system and resulting in an energy consumption level elevated above that associated with the "as new" condition, the method comprising the steps of:
    positioning and orientating a germicidal tube a distance from the surface of the heat exchanger equal to about forty to ninety percent of the light string centerline;
    energizing the germicidal tube to emit sufficient amount of distributed UV radiation to vaporize and remove accumulated organic matter deposited on the surface;
    maintaining energization of the germicidal tube until the accumulated organic matter deposited on the surface is substantially vaporized and removed; and
    operating the heat transfer system, and energizing the germicidal tube to emit sufficient UV radiation to substantially vaporize and remove organic matter subsequently accumulated during operation of the heat transfer system;
    wherein the wavelength of the UV radiation is 253.7 nm and the minimum photon energy striking the surface is 716 mW/cm$^2$ at the closest point of placement to the germicidal tube and not less than 430 mW/cm$^2$ at the farthest point from the germicidal tube;
    whereby energy consumption of the heat transfer system is maintained substantially at the energy consumption level associated with the "as new" condition.

8. The method of reducing energy consumption in a heat transfer system through UVC irradiation of claim 7, the positioning step comprising positioning the germicidal tube a distance from the surface of the heat exchanger equal to about eighty percent of the light string centerline.

9. The method of reducing energy consumption in a heat transfer system through UVC irradiation of claim 8 wherein the surface of the heat exchanger includes plural fins, the positioning step comprising positioning the germicidal tube a distance from the fins equal to about eighty percent of the light string centerline.

10. The method of reducing energy consumption in a heat transfer system through UVC irradiation of claim 7, wherein a germicidal lamp comprises the germicidal tube and further includes a reflector, the method further comprising:
    positioning the germicidal lamp such that the germicidal tube is between the reflector and the heat exchanger, and aiming the reflector toward the heat exchanger.

11. The method of reducing energy consumption in a heat transfer system through UVC irradiation of claim 7 wherein the heat transfer system comprises a cooling system.

12. The method of reducing energy consumption in a heat transfer system through UVC irradiation of claim 7 wherein the heat exchanger comprises a cooling coil.

13. A method of increasing the efficiency of a heat transfer system through UVC irradiation, the heat transfer system comprising a heat exchanger having a surface, the heat exchanger fiber comprising a heat transfer coil including a plurality of spaced fins, the fins being parallel to one another, wherein the heat transfer system has an energy consumption level associated with an "as new" condition, and wherein during the operation of the heat transfer system, organic matter accumulates upon the surface of the heat exchanger, the accumulated organic matter thereby degrading the performance of the heat transfer system and resulting in an efficiency depressed below that associated with the "as new" condition, the method comprising the steps of:

positioning and orienting a germicidal tube, aligning the longitudinal axis of the germicidal tube in a position substantially perpendicular to the parallel planes of the fins so that a UV irradiance level on any point on the surface is sufficient to vaporize and remove organic matter accumulated on the surface when the germicidal tube is energized;

energizing a germicidal tube to emit distributed UV radiation sufficient to vaporize and remove organic matter accumulated on the surface;

maintaining energization of the germicidal tube until the accumulated orgic matter deposited on the surface is substantially vaporized and removed; and operating the heat transfer system, energizing the germicidal tube to emit sufficient UV radiation to substantially vaporize and remove organic matter subsequently accumulated during operation of the heat transfer system;

wherein the wavelength of the UV radiation is 253.7 nm and the minimum photon energy striking the leading edge of the fins is 716 mW/cm$^2$ at the closest point of placement to the germicidal tube and not less than 430 mW/cm$^2$ at the farthest point from the germicidal tube;

whereby the efficiency of the heat transfer system is maintained substantially at the efficiency associated with the "as new " condition.

14. The method of increasing the efficiency of a heat transfer system through UVC irradiation of claim 13, wherein the reflecting and directing of the UV radiaiton received by the heat transfer coil is effected by the reflectivity of UV radiation from the materials from which the heat transfer coil is fabricated, thereby increasing the flux density of the radiation.

15. The method of increasing the efficiency of a heat transfer system through UVC irradiation of claim 13 wherein the heat exchanger reflects and distributes UV radiation around the heat exchanger to thereby increase the dosage of radiation applied to surfaces of the heat exchanger.

16. The method of increasing the efficiency of a heat transfer system through UVC irradiation of claim 13 wherein the heat transfer system comprises a cooling system.

17. The method of increasing the efficiency of a heat transfer system through UVC irradiation of claim 13 wherein the heat exchanger comprises a cooling coil.

18. The method of increasing the efficiency of a heat transfer system through UVC irradiation of claim 13 wherein the heat transfer system comprises a heating system.

19. A method of maintaining efficiency of a heat transfer system through UVC irradiation, the heat transfer system comprising a heat exchanger having a surface, wherein the surface of the heat exchanger includes plural parallel fins, wherein the heat transfer system has an energy consumption level associated with an "as new" condition, and wherein during the operation of the heat transfer system, organic matter accumulates upon the surface of the heat exchanger, the accumulated organic matter thereby degrading the performance of the heat transfer system and resulting in an efficiency below that associated with the "as new" condition, the method comprising the steps of:

providing a germicidal tube, the germicidal tube having a light string centerline;

positioning the germicidal tube a distance from the surface of the heat exchanger equal to about forty to ninety percent of the light string centerline, and orientating the germicidal tube such that the longitudinal axis of the germicidal tube is substantially perpendicular to the parallel fins so that the entire surface is irradiated with UV radiation when the germicidal tube is energized;

energizing the germicidal tube to emit distributed UV radiation sufficient to vaporize and remove accumulated organic matter deposited on the surface; and maintaining energization of the germicidal tube until the accumulated organic matter deposited on the surface is substantially vaporized and removed, and;

operating the heat transfer system, energizing the germicidal tube to emit sufficient UV radiation to vaporize and remove organic matter subsequently accumulated on the surface of the heat exchanger during operation of the heat transfer system;

wherein the wavelength of the UV radiation is 253.7 nm and the minimum photon energy striking the leading edge of the fins is 716 mW/cm$^2$ at the closest point of placement to the germicidal tube and not less than 430 mW/cm$^2$ at the farthest point from the germicidal tube;

whereby energy consumption of the heat transfer system is maintained substantially at the energy consumption level associated with the "as new" condition.

20. The method of maintaining the efficiency of a heat transfer system through UVC irradiation of claim 19, the positioning step comprising positioning the germicidal tube a distance from the surface of the heat exchanger equal to about eighty percent of the light string centerline.

21. The method of maintaining the efficiency of a heat transfer system through UVC irradiation of claim 19 wherein the positioning step comprising positioning the germicidal tube a distance from the fins equal to about eighty percent of the light string centerline.

22. The method of maintaining the efficiency of a heat transfer system through UVC irradiation of claim 19, wherein a germicidal lamp comprises the germicidal tube and further includes a reflector, the method further comprising:

positioning the germicidal lamp such that the germicidal tube is between the reflector and the heat exchanger, and aiming the reflector toward the heat exchanger.

23. The method of maintaining the efficiency of a heat transfer system through UVC irradiation of claim 19 wherein the heat transfer system comprises a cooling system.

24. The method of maintaining the efficiency of a heat transfer system through UVC irradiation of claim 19 wherein the heat exchanger comprises a cooling coil.

25. The method of maintaining the efficiency of a heat transfer system through UVC irradiation of claim 19 wherein the heat transfer system comprises a heating system.

* * * * *

UNITED STATES PATENT AND TRADEMARK OFFICE
CERTIFICATE OF CORRECTION

PATENT NO.     : 6,500,267 B1                                      Page 1 of 1
DATED          : December 31, 2002
INVENTOR(S)    : Forrest B. Fencl and Robert Scheir It is certified that error appears in the above-identified patent and that said Letters Patent is hereby corrected as shown below:

<u>Title page,</u>
Item [73], the assignee should be -- Steril-Aire U.S.A., Inc., Cerritos, CA (US) --

Signed and Sealed this

Fifteenth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,500,267 B1
DATED         : December 31, 2002
INVENTOR(S)   : Fencl et al.

It is certified that error appears in the above-identified patent and that said Letters Patent is hereby corrected as shown below:

Column 15,
Lines 51 and 52, replace "$mW/cm^2$" with -- $\mu W/cm^2$ --.

Column 16,
Lines 44 and 45, replace "$mW/cm^2$" with -- $\mu W/cm^2$ --.

Column 17,
Lines 38 and 40, replace "$mW/cm^2$" with -- $\mu W/cm^2$ --.

Column 18,
Lines 32 and 34, replace "$mW/cm^2$" with -- $\mu W/cm^2$ --.

Signed and Sealed this

Sixth Day of December, 2005

JON W. DUDAS
*Director of the United States Patent and Trademark Office*